(12) United States Patent
Wilkes et al.

(10) Patent No.: US 9,103,788 B2
(45) Date of Patent: Aug. 11, 2015

(54) DETECTION OF BACTERIAL CONTAMINATION IN A SAMPLE

(71) Applicants: The United States of America, as represented by the Secretary, Department of Health and Human Services, Washington, DC (US); Vivione Biosciences, LLC, Jonesboro, AR (US)

(72) Inventors: Jon G. Wilkes, Little Rock, AR (US); Dan Buzatu, Benton, AR (US); Randal Tucker, Hensley, AR (US); Thaddeus John Moskal, Jr., Jonesboro, AR (US)

(73) Assignees: THE UNITED STATES OF AMERICA, AS REPRESENTED BY THE SECRETARY, DEPARTMENT OF HEALTH AND HUMAN SERVICES, Washington, DC (US); VIVIONE BIOSCIENCES, LLC, Jonesboro, AR (US)

( * ) Notice: Subject to any disclaimer, the term of this patent is extended or adjusted under 35 U.S.C. 154(b) by 146 days.

(21) Appl. No.: 13/691,511

(22) Filed: Nov. 30, 2012

(65) Prior Publication Data
US 2013/0137119 A1 May 30, 2013

Related U.S. Application Data

(60) Provisional application No. 61/564,926, filed on Nov. 30, 2011.

(51) Int. Cl.
*G01N 21/64* (2006.01)
(52) U.S. Cl.
CPC ........ *G01N 21/6486* (2013.01); *G01N 21/6428* (2013.01); *G01N 2021/6439* (2013.01); *G01N 2021/6441* (2013.01)
(58) Field of Classification Search
None
See application file for complete search history.

(56) References Cited

U.S. PATENT DOCUMENTS

2006/0223729 A1* 10/2006 Hamblin et al. .............. 510/130
2011/0217694 A1 9/2011 Buzatu et al.

FOREIGN PATENT DOCUMENTS

WO WO 2010/019960 A2 2/2010

OTHER PUBLICATIONS

Omar. Killing of organisms responsible for wound infections using a light-inactivated antimicrobial agent. Ph.D. Thesis, University College London, United Kingdom, 2010.*

Amaguaña et al., "Methods for the Recovery of *Salmonella* spp. From Carboxymethylcellulose Gum, Gum Ghatti, and Gelatin," *J. AOACI* 81:721-726, 1998.
Anonymous, *Escherichia coli* O157:H7 in prepackaged Nestlé Toll House refrigerated cookie dough. *Expert Rev. Anti-Infective Ther.* 7, 641, 2009.
AOAC International, 2006. Final Report and Executive Summaries from the AOAC International presidential task force on best practices in microbiological methodology. www.fda.gov/ucm/groupfds/fdagov-public/@fdagov-foods-gen/documents/document/ucm088702.pdf.
Baier et al., "Singlet Oxygen Generation by UVA Light Exposure of Endogenous Photosensitizers," *Biophys. J.* 91:1452-1459, 2006.
Berdalet and Dortch, "New Double-Staining Technique for RNA and DNA Measurement in Marine Phytoplankton," *Mar. Ecol. Prog. Ser.* 73:295-305, 1991.
Centers for Disease Control and Prevention, "Ongoing Multistate Outbreak of *Escherichia coli* Serotype O157:H7 Infections Associated with Consumption of Fresh Spinach—United States, Sep. 2006," *Morbid. Mortal. Weekly Rep.* 55:1045-1046, 2006.
Cody et al., "An Outbreak of *Escherichia coli* O157:H7 Infection from Unpasteurized Commercial Apple Juice," *Ann. Intern. Med.* 130:202-209, 1999.
Comas and Vives-Rego, "Enumeration, Viability and Heterogeneity in *Staphylococcus aureus* Cultures by Flow Cytometry," *J. Microbiol. Methods* 32:45-53, 1998.
DeRosa and Crutchley, "Photosensitized Singlet Oxygen and Its Applications," *Coordination Chem. Rev.* 233-234:351-371, 2002.
Feng et al., 2011. Bacteriological Analytical Manual, Chapter 4a—Diarrheagenic *Escherichia coli* O157:H7 . Food and Drug Administration, www.fda.gov/food/foodsafety/foodborneillness/foodborneillnessfoodbornepathogensnaturaltoxins/badbugbook/ucm071284.htm.
Food and Drug Administration, 2009. Bad Bug Book BBB—*Escherichia coli* O157:H7 (EHEC) Updated: Jul. 10, 2009 http://www.fda.gov/food/foodsafety/foodborneillness/foodborneillnessfoodbornepathogensnaturaltoxins/badbugbook/ucm071284.htm.
Food and Drug Administration, 2009. Bacteriological Analytical Manual, 8th Edition, Revision A, 1998. Updated: May 14, 2009. www.fda.gov/Food/ScienceResearch/LaboratoryMethods/BacteriologicalAnalyticalManualBAM/default.htm.

(Continued)

*Primary Examiner* — S. Devi
(74) *Attorney, Agent, or Firm* — Klarquist Sparkman, LLP

(57) ABSTRACT

Methods for detecting one or more target bacteria in a test sample are provided. It is shown herein that photosensitizers combined with intense light exposure reduce fluorescing background due to non-bacterial particles. This permits detection of subsequently labeled target bacterial cells (e.g., using a fluorescently labeled antibody) against a largely black background. In particular examples, the methods include incubating the test sample in a growth medium that permits growth of bacteria present in the sample, contacting the sample with a photo-sensitizer; exposing the sample to light under conditions sufficient for the photo-sensitizer to photobleach contaminating non-bacterial particulates present in the sample. The bacteria can then be substantially separated from the sample, thereby generating an isolated bacterial sample. The method can also include contacting the isolated bacterial sample with a binding agent specific for the one or more target bacteria, and detecting the one or more target bacteria.

18 Claims, 8 Drawing Sheets

(56) References Cited

OTHER PUBLICATIONS

Foote, C.S., "Mechanism of Addition of Singlet Oxygen to Olefins and Other Substrates," *Pure Appl. Chem.* 27:635-645, 1971.

Gil et al., "Effect of Postharvest Storage and Processing on the Antioxidant Constituents (Flavonoids and Vitamin C) of Fresh-Cut Spinach," *J. Agric. Food Chem.* 47:2213-2217, 1999.

Green and Durnford, "The Chlorophyll-Carotenoid Proteins of Oxygenic Photosynthesis," *Annu. Rev. Plant Physiol. Plant Mol. Biol.* 47:685-714, 1996.

Hammack et al., "Effectiveness of Universal Pre-Enrichment Broth for Recovery of *Salmonella* from Selected Dairy Foods," *J. AOACI* 86:714-718, 2003.

Hedhammar et al., "A Novel Flow Cytometry-Based Method for Analysis of Expression Levels in *Escherichia coli*, Giving Information About Precipitated and Soluble Protein," *J. Biotechnol.* 119:133-146, 2005.

Henery et al.,. Quantitative Image Based Apoptotic Index Measurement Using Multispectral Imaging Flow Cytometry: a Comparison with Standard Photometric Methods, *Apoptosis* 13:1054-1063, 2008.

Kaprelyants and Kell, "Do Bacteria Need to Communicate with Each Other for Growth?," *Trend. Microbiol.* 4:237-242, 1996.

Krasnovsky, Jr., "Primary Mechanisms of Photoactivation of Molecular Oxygen. History of Development and Modern Status of Research," *Biochem.* 72:1065-1080, 2007.

Kusunoki et al., "Flow Cytometry for the Detection of Enterohaemorrhagic *Escherichia coli* O157:H7 with Latex Beads Sensitized with Specific Antibody," *J. Vet. Med. B* 47:551-559, 2000.

Leach et al., "Same-Day Detection of *Escherichia coli* O157:H7 from Spinach by Using Electrochemiluminescent and Cytometric Bead Array Biosensors," *Appl. Environ. Microbiol.* 76:8044-8052, 2010.

Lindqvist, "Preparation of PCR Samples from Food by a Rapid and Simple Centrifugation Technique Evaluated by Detection of *Escherichia coli* 0157:H7," *Int. J. Food Microbiol.* 37:73-82, 1997.

Maisch et al., "The Role of Singlet Oxygen and Oxygen Concentration in Photodynamic Inactivation of Bacteria," *Proc. Natl. Acad. Sci. U.S.A.* 104:7223-7228, 2007.

McGrath, "Food Emergency Response Network Method Development/Validation/Harmonization," US Food and Drug Administration, www.flworkshop.com/2006/PP4-McGrath_Tim.pdf, 2006.

Metcalf et al., "Enhancement of Erythrosine-Mediated Photodynamic Therapy of *Streptococcus mutans* Biofilms by Light Fractionation," *J. Antimicrob. Chemother.* 58:190-192, 2006.

National Center for Toxicological Research, Presentation on Oct. 19, 2010, before the Science Advisory Board of the National Center for Toxicological Research (NCTR), slide 19 and webpage http://www.fda.gov/AdvisoryCommittees/Calendar/ucm227275.htm.

Oliver, "The Viable but Nonculturable State in Bacteria," *J. Microbiol.* 43:93-100, 2005.

Owens et al. "FERN Level 2 Validation: Assessment of the LITMUS RAPID-B *E. coli* O157 Assay with Nine Product Matrices," Arkansas Department of Health, 2009.

Pathak and Fitzpatrick, "The Evolution of Photochemotherapy with Psoralens and UVA (PUVA): 2000 BC to 1992 AD," *J. Photochem. Photobiol. B.* 14:3-22, 1992.

Rasooly, "Phloxine B, a Versatile Bacterial Stain," *FEMS Immunol. Med. Microbiol.* 49:261-265, 2007.

Rossen et al., "Inhibition of PCR by Components of Food Samples, Microbial Diagnostic Assays and DNA-Extraction Solutions," *Int. J. Food Microbiol.* 17:37-45, 1992.

Snedeker et al, "Primary and Secondary Cases in *Escherichia coli* O157 Outbreaks: A Statistical Analysis," *BMC Infect. Dis.* 9:144, 2009.

Steen, "Flow Cytometry of Bacteria: Glimpses from the Past with a View to the Future," *J. Microbiol. Meth.* 42:65-74, 2000.

Stevens and Jaykus, "Bacterial Separation and Concentration from Complex Sample Matrices: A Review," *Crit. Rev. Microbiol.* 30:7-24, 2004.

Taylor et al., "Effect of Food Matrix and Cell Growth on PCR-Based Detection of *Escherichia coli* O157:H7 in Ground Beef," *J. Food Prot.* 68:225-232, 2005.

Tortorello et al., "Quantitative Analysis and Isolation of *Escherichia coli* O157:H7 in a Food Matrix Using Flow Cytometry and Cell Sorting," *FEMS Immunol. Med. Microbiol.* 19:267-274, 1998.

Uyttendaele et al., "Evaluation of Buoyant Density Centrifugation as a Sample Preparation Method for NASBA-ELGA Detection of *Campylobacter jejuni* in Foods," *Food Microbiol.* 16:575-582, 1999.

Wainwright and Crossley, "Photosensitising Agents—Circumventing Resistance and Breaking Down Biofilms: A Review," *International Biodeterioration & Biodegradation* 53:119-126, 2004.

Weagant and Bound, "Evaluation of Techniques for Enrichment and Isolation of *Escherichia coli* O157:H7 from Artificially Contaminated Sprouts," *Int. J. Food Microbiol.* 71:87-92, 2001.

Wilkes et al. "Reduction of Food Matrix Interference by a Combination of Sample Preparation and Multi-Dimensional Gating Techniques to Facilitate Rapid, High Sensitivity Analysis for *Escherichia coli* Serotype O157 by Flow Cytometry," *Food Microbiol.* 30:281-288, 2012.

Yang et al., "Rapid, Absolute, and Simultaneous Quantification of Specific Pathogenic Strain and Total Bacterial Cells Using an Ultrasensitive Dual-Color Flow Cytometer," *Anal. Chem.* 82:1109-1116, 2010.

\* cited by examiner

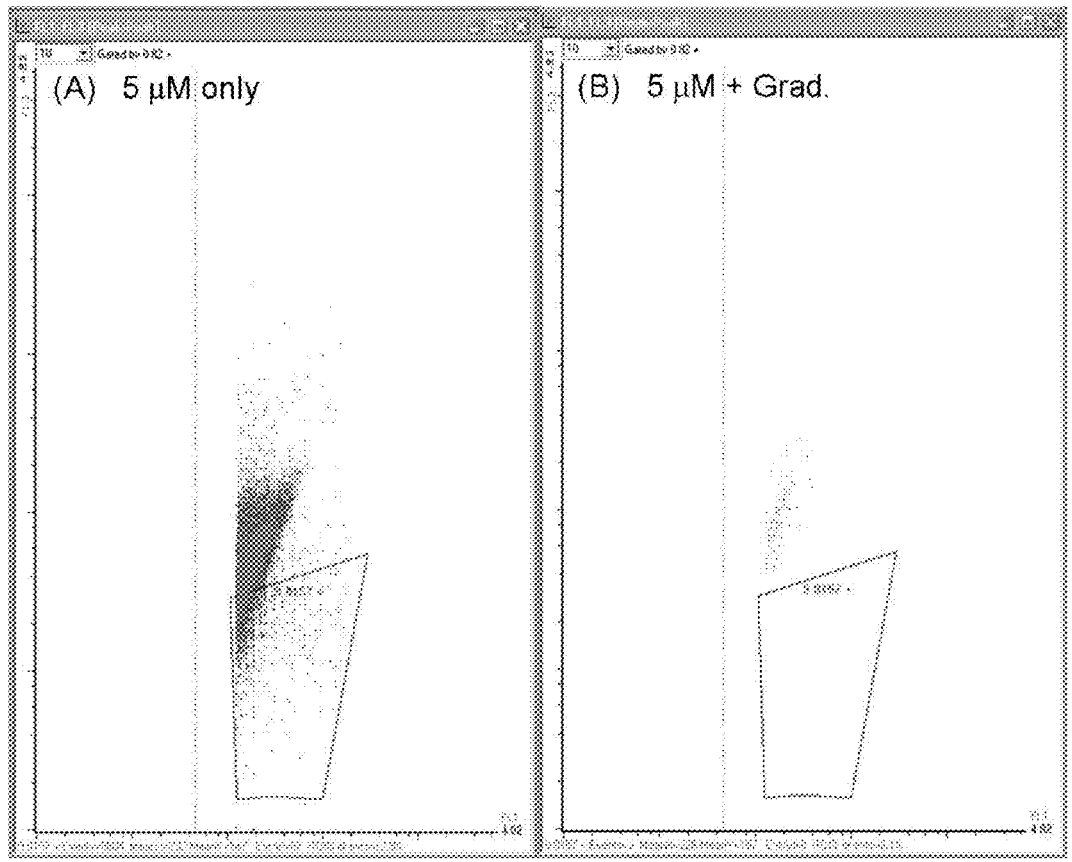
FIG. 7A                                      FIG. 7B

DETECTION OF BACTERIAL CONTAMINATION IN A SAMPLE

CROSS REFERENCE TO RELATED APPLICATION

This application claims priority to U.S. Provisional Application No. 61/564,926 filed Nov. 30, 2011, herein incorporated by reference.

FIELD

This application relates to methods for detecting bacteria present in a sample. Such methods include addition of a photosensitizing agent to the sample and exposing the sample to non-ionizing light, thereby photobleaching non-bacterial particles in the sample, making detection of the bacteria in the sample easier.

BACKGROUND

Because of the pathogenicity of Shiga I and Shiga II toxin producing bacteria (Sandvig, 2001; Cleary, 2004) and multiple recent food borne outbreaks (McCarthy, 1996; Koohmaraie et al., 2007; Cody et al., 1999; CDC, 2006; Denny et al., 2008; Snedecker et al., 2008; Anonymous, 2009; Snedecker et al., 2009) in the United States and abroad involving *E. coli* O157 serovars that produce these toxins, the development of an analytical method for their rapid, specific detection in food is needed. Such a method should have a low cost per sample and be as sensitive as possible because as few as ten *E. coli* O157 cells can cause infection (FDA, 2009a and 2011).

Flow cytometry has been used to measure cellular RNA and DNA content (Berdalet and Dortch, 1991), diagnose health disorders (Muirhead, 1984), determine cell viability (Comas and Vives-Rego, 1998) and quantify protein expression (Hedhammer et al., 2005). The use of flow cytometry to identify food borne pathogenic bacteria, such as *Escherichia coli* serotype O157, has been proposed by several groups (Tortorello et al., 1998; Kusunoki et al., 2000; Leach et al., 2010; Yang et al., 2010). Because of flow cytometry's sensitivity for characterizing individual particles, and its ability to detect target cells (for example to determine their identity and determine if they are viable) without culturing the cells can provide an advantage to other methods, such as PCR which can amplify DNA from non-viable cells (thus making it difficult to distinguish live from dead cells) and also can be inhibited in some food matrices (Rossen, 1992).

For environmental samples that do not have a large amount of background contamination or for applications where an ultralow detection limit is not necessary, a sample can be analyzed in minutes. Flow cytometry measurements can distinguish target bacteria in small numbers from non-target cells and other debris. However, when the application requires finding a few very pathogenic cells, there is the challenge of growing them into a number sufficient to detect and count the population of interest above matrix background. This is the situation for pathogenic *E. coli* O157, especially in food. Analysis of such requires an arsenal of appropriate sample preparation techniques.

The analysis of spinach (*Spinacia oleracea*) is difficult because of background interference (Leach et al., 2010), for example from endogenous chlorophylls, carotenes, iron heme-containing proteins, flavinoids and other biomolecules that absorb and emit light (Green and Durnford, 1996; Gil et al., 1999) in the critical FL1 (green) channel used for enumerating cells. Methods are needed to increase the counts-to-threshold ratio, C/T to enable near-real-time analysis in food with reliable detection of low levels of bacterial contamination. In addition, methods that can be completed within 8 hours, a normal packaging or production plant shift, are needed. Such speed and sensitivity can allow near-real-time QA/QC and not just retrospective determination, results currently available only after multiple plant decontamination cycles.

Most current bacterial diagnostic methods utilize sample volumes between 100 and 500 µL. Small sample volumes, coupled with instrumental limits of detection (LOD) of far more than 1 CFU, require concentration and/or enrichment of samples to facilitate meaningful analysis. As of April, 2010, 21 commercially available rapid analytical methods were performance tested for detection of *E. coli* O157 in one or more foods, including ground beef, apple cider, orange juice, pasteurized milk, spinach, lettuce, and boneless beef trim (AOAC International (2010) AOAC Performance Tested methods. www.aoac.org/testkits/testedmethods.html). Most of these methods specify a selective liquid culture first step designed to depress growth of background microflora while permitting that of the target pathogen (Amaguana et al., (1998) *J. AOACI* 81:721-6; Hammack et al., (2003) *J. AOACI* 86:714-8; DuPont (2010) DuPont Qualicon BAX System Enrichment media for *E. coli* O157:H7MP, www2.dupont.com/Qualicon/en_US/assets/downloads/ BAX %20product %20descrip-Ecolistd.pdf; bioMérieux, Inc. (2009) VIDASC) ECO & VIDAS ICE, Protocol validated by AFNOR AOAC RI Performance Tested[SM] Method Certificate No. 010502, VID-006-09 www.biomerieux-usa.com). The most recent US Food and Drug Administration (FDA) Bacteriological Analytical Manual (BAM) method for *E. coli* O157 specifies a 3 hour first step non-selective enrichment to resuscitate injured target cells followed by enrichment for 20 hours in double-strength tryptone phosphate broth (Feng & Weagant, (2009) US FDA Bacteriological Analytical Manual. Chapter 4a, Diarrheagenic *Escherichia coli*). Growth in liquid media also serves to dilute endogenous food constituents or additives that may inhibit the analysis or otherwise interfere with the assay and to demonstrate by replication that detected target cells are viable. On the other hand, enrichment not only lengthens time-to-results (TTR) but also may not be effective using selective media. In the last fifteen years it has been recognized that bacteria under stress may be "viable but not culturable", retaining the ability to cause disease, even when attempted culture from contaminated food has failed (Oliver, (2005) *J. Microbiol.* 43 (Spec. No.), 93-100).

The FDA evaluated the growth of *E. coli* O157 strains inoculated at low levels (0.12 to 0.42 CFU/g) into alfalfa sprouts and subsequently grown in a variety of selective media typically used at the first stage of analysis by conventional BAM or rapid methods (Weagant & Bound, *Int. J. Food Microbiol.* 71: 87-92, 2001). The results showed that using any of these selective media for recovery of *E. coli* O157 from alfalfa and mixed salad sprouts required a minimum growth period of 24 hours. Attempts to recover target cells in 6 hours failed in many cases. The reasons for the failure included the presence of bacterial growth inhibitors in the sprouts and antibiotics or other bactericides in the selective culture media. In tests not associated with food additives or other environmental stresses, the antibiotics did not depress growth for most strains. When a small number of stressed but viable pathogenic cells were present, there was a significant probability that none would recover and multiply during the shorter period (Kaprelyants and Kell, (1996) *Trend. Microbiol.*, 4:237-242).

SUMMARY

Detecting pathogens in a sample is particularly important and difficult to accomplish when the pathogen to be assayed can cause disease at very low infectious dose, when the sample (such as a food sample) naturally contains a high background of non-pathogenic bacteria, and/or if the product to be assayed is not cooked before consumption. Methods for rapid and accurate detection of low numbers of bacterial cells, for example in foods (such as detection of *E. coli* O157 in salads, peppers, and alfalfa sprouts or detection of *Campylobacter jejuni*, or *Listeria monocytogenes* in ice cream) or other samples (such as environmental and patient samples) are needed.

It is shown herein that photosensitizers combined with intense light exposure reduce the fluorescing background due to non-bacterial particles, thus permitting detection of subsequently labeled target bacterial cells (e.g., using a fluorescently-labeled antibody) against a largely black background. The methods can be completed in less than 8 hours, satisfying the <8 h time-to-results (TTR) goal, and were sufficiently specific, sensitive, and robust. The methods have been validated and compared to Litmus Rapid B protocol and the FDA BAM 4a method for *E. coli* O157:H7 (FDA, 2009b). The disclosed methods produce rapid results and can detect single digit viable bacterial cells (such as single digit viable *E. coli* O157 in 25 g of fresh spinach).

The disclosed methods permit detection of one or more target bacteria in a test sample. For example, the methods can be used to detect a single bacterial type (e.g., detect *E. coli* O157), or multiple different bacteria types (e.g., *E. coli* O157 and *Salmonella* spp.). In some examples, the disclosed methods permit detection of 1, 2, 3, 4, 5, 6, 7, 8, 9, or 10 different bacteria types, for example in the same sample (which can be detected for example simultaneously or contemporaneously).

The methods can include incubating a test sample in a growth medium that permits growth of bacteria present in the sample. This permits the bacteria in the sample to grow and replicate, thus increasing the number of bacteria. The sample is then contacted with a photo-sensitizer, such as phloxine B. The sample is exposed to light (such as non-ionizing light), under conditions sufficient for the light to interact with the photo-sensitizer, thereby producing singlet oxygen radicals such that the contaminating non-bacterial particulates present in the sample are photobleached. The method can include separating the bacteria from the sample, thereby generating an isolated bacterial sample. In some examples, this includes filtration, centrifugation, or combinations thereof. This removes undesirable particles in the sample, such as those that are the same shape and size as the target bacteria, which can interfere with detection of the target bacteria. The method can include contacting the isolated bacterial sample with a binding agent specific for the one or more target bacteria (e.g., antibody), under conditions sufficient for the specific binding agent to bind to the one or more target bacteria. The one or more target bacteria are detected, for example using flow cytometry or microscopy. The sample as determined to contain the one or more target bacteria target bacteria when the specific binding agent is detected (for example by detecting a label associated with the specific binding agent). In some examples, the method further includes determining whether one or more target bacteria detected in the sample are alive or dead (for example by detecting a DNA intercollating dye staining of the bacteria, such as propidium iodide).

In some examples, the disclosed methods are used to analyze a food sample, environmental sample, or patient sample. In some examples, the methods are used to analyze surfaces that come into contact with food (such as equipment in a production or packaging plant), as well as food products.

The foregoing and other objects and features of the disclosure will become more apparent from the following detailed description, which proceeds with reference to the accompanying figures.

BRIEF DESCRIPTION OF THE DRAWINGS

FIG. 3 shows enough background fluorescent counts (51), demonstrating that gradient centrifugation alone is insufficient to eliminate false positive counts.

FIGS. 7A and 7B show two FL1 vs. FL3 fluorescence plot (including the final counting gate in an *E. coli* O157 analysis, shown as a trapezoidal region) for a blank sample of baby food (carrots). (A) With 5-µm pore size filtration alone (6804 qualified events). (B) With 5-µm pore size filtration, followed by buoyancy gradient centrifugation (3 qualified events).

(A) After cleanup and concentration steps, the first gate captured 8172 particles that met initial light-scattering criteria. (B) 225 counted events (each representing a viable *E. coli* O157 cell) clustered in the upper right of the counting region. These originated from approximately eight stressed but viable cells, spiked onto and rubbed into 25 g of fresh spinach.

Figure 10:
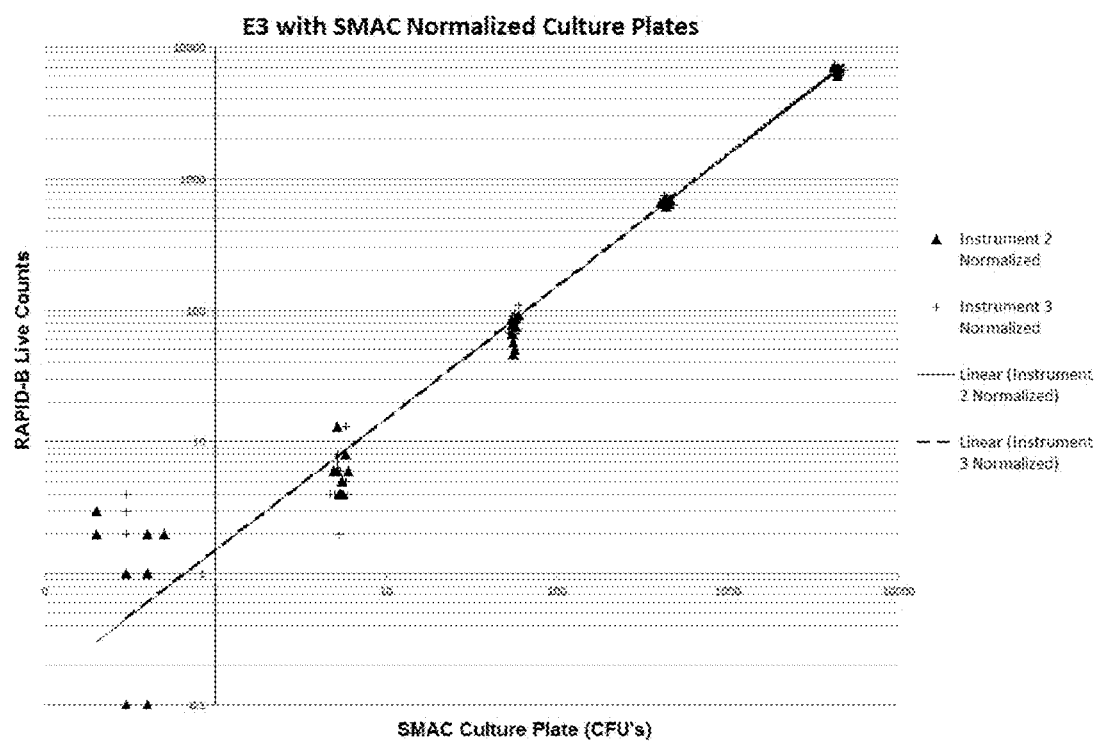

FIG. 10 is a graph showing the comparative linearity for RAPID-B on two instruments and either plate count agar (PCA) or sorbitol-MacKonkey agar (SMAC) CFUs. Linearity is an internal characteristic of a quantitative measure, namely response under dilution, and not by comparison to another method. At the low end of the cell concentration range, the RAPID-B counts lie above the calibration lines.

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

Antibody: A molecule including an antigen binding site which specifically binds (immunoreacts with) an antigen, such as a bacterial antigen. Includes immunoglobulin molecules and immunologically active portions thereof, as well as immunoglobulin-like molecules. Immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In particular examples, a bacteria-specific antibody (such as an antibody specific for *E. coli*) is used to detect the presence of target bacteria in a sample. Antibodies include both monoclonal and polyclonal antibody preparations, as well as chimeric and humanized antibodies.

In some examples, an antibody specifically binds to a target (such as a particular bacterial species) with a binding constant that is at least $10^3$ $M^{-1}$ greater, $10^4$ $M^{-1}$ greater or $10^5$ $M^{-1}$ greater than a binding constant for other molecules in a sample or than a binding constant for other bacterial species. In other examples, an antibody has a Kd value for binding to an antigenic determinant (such as a hapten or epitope) that is on the order of $10^{-6}$ M or lower, such as $10^{-9}$ M or lower, or even $10^{-12}$ M or lower. Kd values can, for example, be determined by competitive ELISA (enzyme-linked immunosorbent assay) or using a surface-plasmon resonance device such as the Biacore T100, which is available from Biacore, Inc., Piscataway, N.J.

Antibody fragments include proteolytic antibody fragments [such as F(ab')2 fragments, Fab' fragments, Fab'-SH fragments and Fab fragments], recombinant antibody fragments (such as sFv fragments, dsFv fragments, bispecific sFv fragments, bispecific dsFv fragments, diabodies, and triabodies), camelid antibodies (see, for example, U.S. Pat. Nos. 6,015,695; 6,005,079; 5,874,541; 5,840,526; 5,800,988; and 5,759,808), and antibodies produced by cartilaginous and bony fishes and isolated binding domains thereof (see, for example, International Patent Application No. WO03014161).

Binding affinity: Affinity of an antibody or antigen binding fragment thereof for an antigen. For example, under designated conditions, an antibody that binds preferentially to a particular target bacterium (such as *E. coli*) and does not bind in a significant amount to other proteins or polysaccharides present in the sample (or to other bacterium), is referred to an antibody that specifically binds to its target. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

Contact: To bring one agent into close proximity to another agent, thereby permitting the agents to interact. For example, an antibody (or other specific binding agent) can be applied to a test sample, thereby permitting detection of bacteria in the sample that are specific for the antibody. Similarly, a photosensitizing agent can be added to a test sample, thereby permitting photobleaching of autofluoresceing particulates in the sample.

Detect: To determine if an agent (such as a bacterium) is present or absent. In some examples this can further include quantification. For example, use of the disclosed methods permits detection of one or more target bacterium, such as by flow cytometry or fluorescence microscopy. Detection can be in bulk, so that a macroscopic number of molecules can be observed contemporaneously or simultaneously. Detection can also include detection of single events, such as a single bacterium.

Fluorophore: A chemical compound, which when excited by exposure to a particular stimulus such as a defined wavelength of light, emits light (fluoresces), for example at a different wavelength.

Examples of particular fluorophores that can be used in the methods disclosed herein (for example to detect antibody-bacteria binding interactions) include but are not limited to those disclosed in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron© Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. In one example the fluorophore is a cyanine dye, such as Cy3 or Cy5.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Molecular Probes (Eugene, Oreg.).

In one example, the fluorophore is a quantum dot (e.g., QDOT®).

Growth Medium: A liquid or gel that permits and supports the growth of microorganisms, such as bacteria. Includes nutrient broths that contain components necessary for bacterial growth and replication, such as water, a carbon source (such as glucose) and salts. Such media can include other agents, such as vitamins and amino acids.

Isolated: An "isolated" biological component (such as a bacterial cell(s)) has been substantially separated, produced apart from, or purified away from other components in the sample in which the bacterial cells occur, such as, other cells, nucleic acids, proteins, and autofluorescent particles (e.g., fluoresce at 300 to 700 nm, such as 450 to 700 nm, or 488 nm). Bacterial cells which have been "isolated" thus include cells purified by standard purification methods, such as filtration and centrifugation. The bacteria need not be 100% pure, but includes bacteria where at least 50% of the other materials in the sample have been separated away from the bacterial cells, such as at least 75%, at least 80%, at least 90%, or at least 95% of the other materials in the sample have been separated away from the bacterial cells in the sample.

Label: A detectable compound or composition that is conjugated directly or indirectly to another molecule, such as an antibody or other specific binding agent, to facilitate detection of that molecule. Specific, non-limiting examples of labels include fluorescent tags, enzymatic linkages, and radioactive isotopes. In some examples, an antibody is labeled, such as directly or with a labeled secondary antibody, thus permitting detection of the antibody (and the bacterium to which the antibody is bound). Other exemplary labels include quantum dots, gold particles, quantum spheres and the like.

Sample: A material to be analyzed, for example to determine if it contains one or more target bacteria. Includes but is not limited to biological samples (e.g., obtained from a human or veterinary subject); food samples (e.g., vegetable, fish, dairy, fruit or meat sample); environmental samples (e.g., soil, air, water, surfaces), and the like.

Specific binding agent: An agent that binds substantially only to a defined target. Thus a protein-specific binding agent binds substantially only the defined protein, or to a specific region within the protein. As used herein, a specific binding agent includes antibodies, aptamers, PNAs, and other agents that bind substantially to a specified target, such as a bacterial peptide or DNA sequence. The determination that a particular agent binds substantially only to a specific peptide can readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Target bacteria/bacterium: A bacterium whose detection is intended. The target can be for instance a bacterium known to infect a human or veterinary subject, food, or the environment. In one example, a target bacterium is one that causes disease in a human or veterinary subject (referred to in the art as a pathogenic bacterium).

Under conditions sufficient for: A phrase that is used to describe any environment that permits the desired activity. In one example, includes incubating a sample in a growth or culture medium sufficient to allow the bacteria to grow and replicate. In particular examples, the desired activity is photobleaching undesired particulates in a sample, for example by use of a photosensitizing agent and light.

Overview

Recent instrumental improvements, data filtering techniques, and fluorescence tagging strategies have facilitated the use of flow cytometry to detect in real time or near real time the presence of bacterial cells in food, clinical, and other matrices. Combined, these allow very specific determination of each detected bacterium cell's identity (e.g., serotype level specificity) and state (e.g., spore or vegetative cell, viable or nonviable). However, these methods are complicated whenever the expected signals for the targeted bacterium and the detected events deriving from the food or other sample matrix, coincidentally produce the same designated light scatter and emission profile. For example, food particles can exhibit natural fluorescence and may be similar in size to the target bacterium. This leads to false positive analyses. Although the extent of the problem varies with the particular type of sample, it is problematic enough to cause false positive results for low levels of bacteria in some samples, such as food samples (e.g., ground beef, raw cookie dough, raw spinach, jalapeno peppers, tomatoes, milk and other foods responsible for foodborne pathogen outbreaks).

It is shown herein that using photo-activated sensitizers, intense non-ionizing light photo-exposure (e.g., visible light from either a polychromatic or a monochromatic source of wavelength corresponding to the absorbance maximum of the photosensitizer), mild detergents (e.g., TWEEN® 20 or TWEEN® 80), acidity buffering (conditions the bacterial cells so the epitopes do not stick to the cell walls), and centrifugation with decanting (to wash out the photosensitizer), and optional free radical quenching reagents (to diminish effect of the photo sensitizer), the photo-bleaching of the particle colors can be achieved prior to introducing the fluorescent tags and fluorescent viability reagents used for flow cytometric detection of target analytes or reagents used for other types of analysis.

Once a method was developed that met the <8 h TTR milestone and was sufficiently sensitive, attempted independent laboratory validation followed. The goal was to detect as few as 4 viable cells of *E. coli* O157 in 25 g of fresh spinach (an average of 0.16 CFUs per gram). Results were compared to parallel sample analyses using the FDA Bacteriological Analytical Manual (BAM) 4a method for *E. coli* O157:H7 (Feng et al., 2011). The first method was only partly successful, results detailed in Example 2.

An improved sample handling method was devised for reducing background fluorescence, enhancing analytical sensitivity, and increasing reliability and accuracy of results, while retaining the desired characteristics of high speed, low cost, high sensitivity and utility for QA/QC in a packaging environment or screening in regulatory contexts. Typical first method results (Example 2) when compared to those from experiments during method development (Example 4) illustrate the improvement contributed by the added preparation techniques, particularly photobleaching.

In addition, external validation was repeated to specify very low level target cell inoculations. The improved method included a few experimental variations and a couple of added techniques. (The experimental variations are reported in Example 1 and a summary of results in Example 5).

Another feature of the improved method was that, even after photobleaching, assessment of cell viability was possible. Cell non-viability is indicated by permeation through the cell membrane of an FL3-fluorescing (red) DNA dye normally excluded when the membrane is intact (Comas and Vives-Rego, 1998). Flow cytometric events attributable to dead cells thus appear at greater intensity in the FL3 dimension of the FL1 vs. FL3 dot plot used for cell enumeration. In the case of photobleaching with phloxine B sensitizer, it proved possible to treat the spinach matrix effectively without rupturing most target cell membranes, so that viability could still be corroborated.

The ultimate method was subject to FERN Level 2 external laboratory validation. This validation used three spiking levels (high, low, blank=122, 15, or 0 cells/25 g spinach), none of which showed evidence of method breakdown. A second test of the improved method used only two levels (very low, blank; 4 or 0 cells/25 g spinach, respectively). The latter explored the absolute sensitivity of the method for low single digit target cell contaminations. The validation study and very low level tests were executed by FDA microbiological staff with minimal experience using the RAPID-B system. Results would therefore represent the system's likely performance in the field. Separate from external laboratory testing, the method limit of detection (LOD) was determined in experiments conducted by RAPID-B technical experts.

The present disclosure provides novel methods for the rapid detection of bacteria in a sample, such as low levels of Shiga toxin-producing *Escherichia coli* serotype O157 in food samples. The methods include short-term enrichment of the target bacteria (e.g., incubation for at least 4 or at least 5 hours in growth media at a temperature of least 30° C.) followed by photobleaching of autofluorescence of cellular debris or other particulate using a photo-sensitizer (e.g., phloxine B) and light. The resulting bacterial cells can be separated from the sample (e.g., concentrated), for example by filtration and/or centrifugation to increase the target bacterial cell to background event ratio in the two dimensional fluorescence gate used for target determination. In some examples, the sensitivity of the method is one bacterial cell per 100-200 μl analyzed volume. In some examples the time-to-results (TTR), was 8 hours or less, such as no more than 8 hours, no more than 7 hours, no more than 6 hours, or no more than 5 hours, such as 4 to 6 or 4 to 8 hours. Thus, the disclosed methods provide fast analysis time, low cost per sample, high sensitivity, and high specificity.

In one example, a robust method with high sensitivity for rapid analysis of *E. coli* O157 on food, such as raw spinach (*Spinacia oleracea*), is provided. Using a 5 hour non-selective enrichment of artificially inoculated samples, followed by photobleaching with phloxine B as a photosensitizer and brief intense light exposure before the addition of reagents and incubation, resulted in reduced sample background and a much lower threshold for expert analysts (from ~50 to either 11 in the validation or 6 in the follow-up test). Use of gradient centrifugation excluded about 98% of the residual spinach particle load. Sample preparation improvements resulted in a method that retained both analytical integrity (correctly detecting the targeted cells and distinguishing their viability state even after photobleaching) and target cell specificity. RAPID-B detected, without prior target isolation, single digit cell counts of *E. coli* O157 contamination in spinach. In external laboratory validation, RAPID-B and the reference method both correctly detected *E. coli* O157 at inoculations of 122 or 14 cells per 25 g spinach. In a follow-up study, after inoculations of four or zero cells per 25 g and 6 hour enrichment, RAPID-B correctly identified 92% of 25 samples. The RAPID-B method limit of detection ($LOD_{RAPID-B}$) was one target cell in 150 g of spinach. Thus, the disclosed flow cytometry system with the sample handling method using phloxine B photobleaching met criteria for fast analysis and low cost per sample with high confidence and high specificity.

A validation study, conducted to Food Emergency Response Network (FERN) Level 2 standards is also presented herein. The disclosed RAPID-B™ method was assessed for its ability to detect *E. coli* O157 by enrichment from nine food matrices. An overnight incubation step was used for both flow cytometric and reference methods. The samples were subsequently diluted 1:10,000 to reduce food matrix interference. Since the *E. coli* could still be detected following the 10,000 dilution, it was inferred that full 24 hour enrichment was not necessary.

Recovering low levels of *E. coli* O157 cells from 25 g samples of ground beef following an abbreviated 5 hour enrichment confirmed that much shorter time-to-results (TTR) was possible (by reducing enrichment time without sacrificing sensitivity). Data acquisition strategies and sample treatments that reduced analytical interferences and are applicable to many foods are provided herein.

Methods of Detecting Bacteria

The present disclosure provides methods of detecting one or more target bacteria in a sample, for example using flow cytometry or microscopy (such as fluorescence microscopy). Exemplary samples include, but are not limited to, a food sample, patient sample, or environmental sample. In a specific example, the sample is a food sample that includes a vegetable, meat, dairy item, fruit, juice, or peanut butter.

In some examples, the method includes incubating the test sample in a growth medium under conditions that permit growth of bacteria present in the sample. This can also allow the bacteria to replicate, thereby increasing the number of bacteria in the sample. This can be desirable, for example when only a few, such as a single bacterium, are present, as this makes it easier to detect the target bacteria in the test sample. Growth medium appropriate for growing particular target bacteria are known in the art, and in some examples includes brain heart infusion (BHI) media or tryptic soy broth (TSB). In some examples, incubating the sample in the growth medium includes incubation at a temperature of at least 25° C., such as 25° C. to 45° C. or 37° C. to 45° C., for at least 4 hours (such as at least 5 hours, at least 6 hours, at least 7 hours, or at least 8 hours, such as 4 to 6 hours or 4 to 8 hours).

The method can also include contacting the test sample with a photo-sensitizer (such as phloxine B) and exposing the sample to light (such as non-ionizing light), under conditions sufficient for the production of singlet oxygen radicals and photobleaching of contaminating non-bacterial particulates present in the test sample. In some examples, the isolated bacterial sample is exposed to light at a light intensity of at least 5,000 LUX, at least 10,000 LUX, at least 20,000 LUX, at least 30,000 LUX, or at least 40,000 LUX. In some examples, the isolated bacterial sample is exposed to at least 1,000 lumens, at least 10,000 lumens, or at least 25,000 lumens. In particular examples, the light is infra-red, visible, or UV light.

The bacteria can then be separated from the sample, for example concentrating the bacteria, thereby generating an isolated bacterial sample. Methods for separating bacteria from a sample are known in the art, and can include pelleting the bacteria, filtering the sample (e.g., such that bacteria pass through the filter, but smaller particles are retained in the filter), centrifugation of the sample (e.g., using gradient centrifugation), or combination thereof.

The method can include contacting the isolated bacterial sample with a specific binding agent specific for the one or more target bacteria, under conditions sufficient for the specific binding agent to bind to the one or more target bacteria (for example to generate a specific binding agent-bacterium complex). Exemplary specific binding agents include but are not limited to antibodies specific for a target bacterium and aptamers or peptide nucleic acids (PNAs) specific for a target bacterium. In some examples, the specific binding agents are directly labeled, for example with a fluorophore, thus permitting direct detection of a specific binding agent-bacterium complex. In other examples, the specific binding agent-bacterium complex is detected using a secondary agent, such as a labeled secondary antibody that binds to the specific-binding agent. The method can further include contacting the isolated bacterial sample with a mild detergent, for example under conditions that permit the detergent to expose epitopes on the bacterial cell surface.

The one or more target bacteria are detected, for example by using flow cytometry or microscopy to detect the labeled specific binding agent-bacterium complexes. The sample can be designated as containing the one or more target bacteria target bacteria when the specific binding agent-bacterium complex is detected, for example by detecting a label directly or indirectly associated with the specific binding agent. Detection can be qualitative (e.g., the target bacterium is present or not), quantitative (e.g., 10 target bacterium were detected), or combinations thereof.

In some examples, the method further includes determining whether one or more target bacteria detected in the sample are alive or dead. For example, the method can include contacting the isolated bacterial sample with propidium iodide (PI) or other agent that penetrates dead cells, wherein the presence of detected PI indicates that the cell is dead.

In particular examples, the method permits detection of low-levels of contamination, such as detection when less than 30 target bacteria are present in the sample, such as less than 25, less than 20, less than 15, less than 10, or less than 5 bacteria, such as 1 to 30, 1 to 20, 1 to 10, 2 to 30, 2 to 10, or 2 to 5 bacteria, or 1, 2, 3, 4, 5, 6, 7, 8, 9, or 10 bacteria are present in the sample.

In particular examples, the methods provided herein have a sensitivity of at least 90%, at least 95%, at least 98%, at least 97%, or at least 99%, wherein sensitivity is the probability that a statistical test will be positive for a true statistic. In particular examples, the methods provided herein have a specificity of at least 90%, at least 95%, at least 98%, at least 97%, or at least 99% specificity.

In some examples, the method is completed and detects bacteria present in a sample within 8 hours, such as in no more than 7 hours, or no more than 6 hours, no more than 5 hours, or no more than 4 hours, such as 5 to 8 hours or 5 to 6 hours. That is, the method has time-to-results (TTR) of no more than 8 hours, such as in no more than 7 hours, or no more than 6 hours, no more than 5 hours, or no more than 4 hours, such as 4 to 8 hours, 4 to 6 hours, 5 to 8 hours, or 5 to 6 hours.

I. Exemplary Samples

A sample includes material known or suspected of containing a pathogen, such a target bacterium.

In one example, the sample is a biological sample, such as one obtained from a subject. Exemplary subjects include human and veterinary subjects, such as mammals (e.g., cats, dogs, rodents, cows, pigs and chickens) and other animals (e.g., fish, birds, and crustaceans). Biological specimens can include nucleic acid molecules (for example genomic DNA, cDNA, RNA, or mRNA) and/or proteins. As used herein, biological samples include clinical samples, such as those containing cells, tissues, and bodily fluids, obtained from the subject such as: biopsied or surgically removed tissue (e.g., biopsy samples such as a fine needle aspirate, a core biopsy sample, or an excisional biopsy sample), blood or a fraction thereof (such as plasma or serum), urine, feces, saliva, swabs (such as oral, nasal, skin, ear, or vaginal swabs), amniocentesis samples and autopsy material.

In one example the sample is a food sample, such as one suitable for human or veterinary consumption. In some examples, such food products are difficult to analyze because of biochemical and/or opticalinterference. Food matrices that are difficult for flow cytometry are so classified because they produce large numbers of particles in the size range of bacteria. In addition, these particles autofluoresce, producing signals that can mimic the signal from the target bacteria. Specific examples include a vegetable sample (such as one containing spinach, lettuce, carrot, cucumber, tomato, jalapeno or other pepper, alfalfa sprouts, broccoli, corn, or combinations thereof, such as a bagged salad); meat sample (such as one that includes chicken, pork, beef, turkey, buffalo, or lamb, or combinations thereof, for example a ground meat sample, hot dogs, sausage, salami or beef muscle); fish sample (such as shellfish, salmon, trout, flounder, and the like), fruit sample (such as one that includes cantaloupe (or other melon, such as watermelon), grapes, apples, oranges, strawberries, blueberries, or combinations thereof); a sample containing a dairy item (such as those containing eggs, milk, or cheese, for example mayonnaise or ice cream), a juice sample (such as one containing apple juice, orange juice, cranberry juke, grape juice, pomegranate juice, pear juice, or combinations thereof), peanut butter, nut meat, cookie dough, condiments (such as horseradish sauce, ketchup, tartar sauce, and the like), and baby food.

In another example, the sample is an environmental sample, such as a soil, air, water, or surface sample (such as a swabbed surface). For example, an environmental sample includes a surface that has been swabbed or other method used to collect bacteria or other microbes that may be present on the surface. Exemplary surfaces include floors, countertops, walls, and equipment (such as surfaces found in food processing and packaging plants).

Samples can be collected by methods known in the art, and can include the use of swabs and spatulas. In some examples, samples are collected into containers, such as samples that are in liquid or gas form.

In some examples the samples are used directly. However, the samples can be processed before they are analyzed. Samples can further processed to make the sample more amenable to the disclosed methods. For example, the samples may be liquefied, pulverized, crushed, chopped, diluted, concentrated, filtered, stomached, pulsified, sonicated, or combinations thereof prior to their analysis. In some examples, the sample is incubated on, or in, a growth medium that permits growth of bacteria that may be present in the sample (see discussion below).

In some examples, the pH of the sample is lowered prior to analysis, to aid in removal of undesired proteins. For examples, proteins in samples may bind non-specifically to various probes used to detect target bacteria and lead to generation of false positive results. Examples of high protein content samples include, but are not limited to: milk, peanut butter, cell lysates, saliva, urine, blood, and related materials. In some examples, high-protein containing samples are treated by: lowering the pH of the sample to cause at least some of the proteins in the sample to curdle (e.g., by adding an acidic solution, such as 10% acetic acid) and filtering the curdled sample on to one or more filters that are permeable to the target bacteria (e.g., a polycarbonate filter having pore sizes ranging from about 5 μm to about 8 μm.). Suitable curdling pH ranges can vary for different samples. For instance, a milk sample may curdle in at a pH of about 4.7 to about 4.2. The time period for curdling to occur may also vary for different samples. For instance, such time periods may vary from about 1 minute to about 5 minutes for high protein samples such as milk. The method can further include re-filtering the sample onto a filter that captures the target bacteria; immersing the filter in a liquid; and optionally vortexing the filter to dissociate the microbes into the liquid (such as a buffer, e.g., 1×PBS).

In some examples, the sample is treated with one or more detergents or surfactants, for example in order to remove or substantially reduce the presence of particles that may interfere with the analysis. Exemplary particles include fluorescent oil droplets and other autofluorescent particulates. Suitable detergents include without limitation and in various combinations, polyethylene glycol, EDTA, Triton-100®, Tween®-80, Tween®-20, sodium dodecyl sulfate (SDS), and the like. In some examples, the sample is treated with a detergent in solution at a concentration from about 0.01% by weight to about 5% by weight of the solution. In other examples, such concentration ranges may vary from about 0.1% by weight to about 5% by weight of the solution. In still other examples, such concentration ranges may vary from about 3% by weight to about 5% by weight of the solution. In various examples, a solution may include from about 0.1% by weight to about 5% by weight of Tween®-80 or Tween 20. The samples can be treated with one or more detergents for various periods of time that are sufficient for eliminating or substantially reducing the presence of background particles and other interferences, for example from about 30 seconds to about 120 minutes, such as 1 minute to 5 minutes or 1 minute to 20 minutes.

II. Treatment of Samples

A. Culturing of Bacteria in the Sample

In some examples, the methods include incubating the sample in a growth medium, which permits growth of the target bacteria that may be in the sample. In some examples, this also permits replication of the bacteria, thereby increasing the number of target bacteria in the sample, which makes the target bacteria easier to detect. The growth medium selected should be one that permits growth of the target bacteria. In specific examples, the growth media is a liquid medium, which includes a carbon source, salts, and nutrients and optionally antibiotic(s). Exemplary growth media includes, but is not limited to: brain heart infusion (BHI) media, tryptic soy broth (TSB), and MacConkey medium. In one example, the target bacterium is *E. coli* and the growth medium is BHI. In another example, the target bacterium is *Salmonella* spp., *Campylobacter jejuni*, *Listeria monocytogenes*, or *Staphylococcal* spp. and the growth medium is TSB. In another example, the target bacterium is *Vibrio* spp. and the growth medium is alkaline saline peptone water (ASPW).

The sample is incubated in the growth medium under conditions that permit bacteria present in the sample, which may include the one or more target bacteria, to grow and increase in number. The conditions include incubation at an appropriate temperature and for a time that permits the bacteria to grow and replicate. In some examples, the sample is incubated in the growth medium at a temperature of at least 25° C., at least 30° C., at least 37° C., at least 40° C., or at least 45° C., such as 25° C. to 50° C., 25° C. to 45° C., or 37° C. to 45° C. One will appreciate that thermophilic bacteria could grow at even higher temperatures (such as at least 45° C., at least 60° C., or at least 80° C., such as 45° C. to 122° C.) and that psychrophilic bacteria could grow at even lower temperatures (such as below 15° C., below 10° C., or below 4° C., such as −15° C. to +10° C.).

In some examples, the sample is incubated in the growth medium for at least 2 hours, at least 3 hours, at least 4 hours, at least 5 hours or at least 6 hours, such as 2 to 10 hours, 2 to 5 hours, 4 to 6, or 3 to 5 hours. In some examples, the sample is incubated in the growth medium for longer periods, for example if the bacterium grows slowly, such as *Mycobacterium tuberculosis*, such as at least 24 hours, at least 48 hours, at least 96 hours, at least one week or least two weeks, such as 24 hours to 1 month.

B. Addition of Photo-Sensitizing Agent and Photobleaching

Although centrifugation and filtering of the sample can reduce the number of particles in the sample that interfere with detecting the target bacteria (see discussion below), such methods are not completely effective. Autofluorescent particles remain, making analysis of the sample difficult. For example, some samples contain compounds having conjugated systems, such as carotenes, chlorophylls, and/or heme proteins, which autofluoresce. Samples that are difficult for flow cytometry are so classified because they produce large numbers of particles in the size range of bacteria and these particles also autofluoresce to give signals that can mimic the target bacteria. Typically such particles occur in a wide range of sizes. The light scatter and fluorescence profiles differ according to the sample.

The inventors have determined that the fluorescence of the contaminating non-bacterial particles can be significantly reduced or eliminated. However, ideally agents that reduce or eliminate autofluorescence do not disrupt bacterial cell membranes, as the methods not only detect bacteria, but in some examples also determine whether the bacteria detected in the sample are alive or dead. Thus, chemical bleaches (such as hydrogen peroxide, sodium carbonate, and sodium hypochlorite) have been shown to be ineffective.

Thus, after incubation of the sample in the growth medium but before addition of the specific binding agents (specific for the one or more target bacteria), one or more photo-sensitizers are contacted with (for example added to) the sample. The prefix "photo" connotes a phenomenon in which the effective reactivity of infra-red, visible, UV or other non-ionizing radiation (called here "light") is increased by addition to the sample of the photo-sensitizer that interacts with the light radiation to produce singlet oxygen. The activity is based on production of the singlet oxygen in a manner that can be controlled as to intensity and duration (in a way that hydrogen peroxide or other aggressive reagents cannot). Exemplary control elements for exposure include (a) the amount of sensitizer added to the sample (e.g., 1 to 15 microliters of 0.5% phloxine B), (b) the wavelength and intensity of the incident light (e.g., visible spectrum from 380 nm to 750 nm), (c) the identity of the sensitizer and its corresponding maximum absorbance frequency (e.g., for phloxine B its absorption maximum is about 570-590 nm), and (d) exposure duration (e.g., 1 minute to 30 minutes).

The photo-sensitizing agent in some examples is non-chemically reactive and non-toxic to the target bacteria. However, the photosensitizer need not be completely non-toxic to the target bacteria, as long as such toxicity is not immediate (e.g., the target bacteria are not killed within one hour of adding the appropriate amount of photosentizing agent). As shown herein, even if the bacteria are eventually killed by the photo-sensitizing, rapid determination of their viability in the flow cytometer can be conducted before the cell membranes (and cell surface epitopes) have deteriorated. Consequently, the bacteria are counted by cytometric analysis as "live," if that was their viability state before the photo-bleaching.

In some examples, the sample is incubated with the photosentizing agent (e.g., phloxine B) for at least 30 seconds, such as at least 1 minute, or at least 5 minutes, for example from 30 seconds to 60 minutes or 5 minutes to 30 minutes.

The result of this treatment process is to dramatically reduce or eliminate matrix interference, significantly lower detection limits, and significant time-to-results reduction. In some examples, the method includes post photo-bleaching quenching of the free radical producing agent (for example by addition of cysteine or other sulfur-containing organic compound), so as to enable subsequent handling of the sample in modest light conditions without concern that the residual sensitizer could bleach out the analytical signal (the fluorescent tags or other reagents added (after photobleaching) for detecting the target bacteria).

Exemplary photo-sensitizing agents that can produce singlet oxygen include visible spectrum photo-sensitizing agents such as green fluorescent protein (GFP), rose bengal, erythrosine B, phloxine B, and eosin YS; near IR spectrum photo-sensitizing agents such as phthalocyanines and naphtalocyanines; or UVA photo-sensitizers such as psoralenes, riboflavin, flavin mononucleotide, and flavin adenine dinucleotide.

In particular examples, the photo-sensitizing agent comprises phloxine B. The structure of phloxine B is shown below.

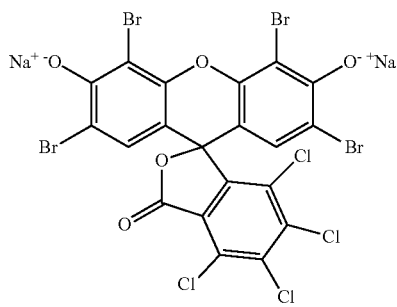

After addition of a non-chemically reactive and non-toxic photo-sensitizing agent (such as at least 1 µl of a 0.5% phloxine B solution, such as at least 5 µl at least 10 µl, or at least 15 µl of a 0.5% phloxine B solution, for example 1 to 15 µl of a 0.5% phloxine B solution), the sample is exposed to intense light, thereby increasing the photobleaching of non-bacterial contaminating particles. For example, samples can be exposed to visible light, such as a visible spectrum from 380 nm to 750 nm, such as 570 nm to 590 nm. In some examples, the sample is exposed to a light intensity of at least 1,000 LUX, at least 10,000 LUX, at least 20,000 LUX, at least 30,000 LUX, at least 40,000 LUX, such as 1,000 to 10,000 LUX, 1,000 to 24,000 LUX, 10,000 to 50,000 LUX, or 1,000 to 50,000 LUX. In some examples, the isolated bacterial sample is exposed to at least 1,000 lumens, at least 10,000 lumens, at least 25,000 lumens, or at least 50,000 lumens, such as 1,000 to 5,000 lumens 1,000 to 25,000 lumens, or 1,000 to 50,000 lumens. Singlet oxygen from phloxine B (or other photo-sensitizer) generated during light exposure reacts with the conjugated π orbitals in autofluorescent compounds. This treatment does not immediately rupture bacterial cell membranes.

In some examples, after photobleaching the sample, the sample is exposed to one or more agents that can deactivate the photo sensitizer, such as exposure to ultraviolet light for a sufficient period of time to deactivate the photosensitizer (e.g., at least 1 millisecond, at least 0.25 seconds, at least 0.5 seconds, at least 1 minute, or at least 5 minutes). In some examples, the photosensitizer is deactivated by incubation of the sample at room temperature for a sufficient period of time (e.g., at least 1 minute, at least 5 minutes, at least 10 minutes, at least 30 minutes, or at least 60 minutes, such as 10 minutes to 60 minutes). In some examples, the sample is treated with a chemical reducing agent, such as glutathione, mercaptoethanol, DTT, a sulfhydryl-containing compound (e.g., cysteine).

C. Separating the Bacteria from the Sample

In some examples, after incubating the sample in the growth medium and with the photo-sensitizing agent, the bacteria in the sample are substantially separated away from the sample, for example by centrifugation, filtration, or combinations thereof. This can result in concentration of the bacteria.

In some examples, the bacteria in the sample are pelleted, for example using centrifugation, and the resulting pellet used in further analysis. In some examples, after isolating the bacteria from the sample, the resulting isolated bacterial sample (such as a re-suspended bacterial pellet) can be filtered, for example to remove contaminating particles that are not bacteria (such as autofluorescent particles). In particular examples, the sample is filtered through a material containing pores that allow the target cells to pass through, for example with 0 to 90% efficiency. Thus, in some examples, the sample is filtered through a material containing pores that are no more than 50 µm in diameter, such as no more than 25 µm in diameter, no more than 25 µm in diameter, no more than 10 µm in diameter, no more than 1 µm in diameter, or no more than 0.1 µm in diameter, for example a material containing pores that are 0.1 to 50 µm in diameter, 1 to 10 µm in diameter, or 1 to 5 µm in diameter, such as 5 µm PVDF. In one example, the sample is first filtered through a material with larger pores, then through a material with smaller pores, for example to reduce clogging. For example the sample can be filtered first through a material with pores of at least 10 µm in diameter (e.g., at least 20 µm in diameter, such as 10 to 20 µm in diameter, 10 to 30 µm in diameter or 20 µm in diameter) (for example using a vacuum), then through a material with pores of no more than 9 µm in diameter (e.g., no more than 8 µm in diameter, such as 1 to 8 μm n diameter, 0.5 to 5 μm in diameter, or 5 μm in diameter), for example using a syringe filter.

In some examples, gradient centrifugation is used to separate the target bacteria from the majority of contaminating particles in the sample that are not bacteria (such as autofluorescent particles). Such separation techniques are routine. For example, in some examples, at least 50%, at least 75%, at least 80%, or at least 90% of the contaminating particles are removed. This results in bacteria that are substantially isolated from the sample. In some examples, the sample is filtered prior to gradient centrifugation.

In some examples, such as for a sample containing milk-based and other fat products, the sample is curdled by addition of 0.1% HCl to produce two separate layers: a bacteria-containing aqueous lower layer and a fatty upper layer. The bacteria-containing aqueous lower layer can be recovered for further analysis. This step can be performed before or after the photobleaching step.

In some examples, the sample (such as one that is solid or semi-solid) is subjected to pre-filtration treatments, such as one or more of: dilution with a liquid (such as PBS) followed by blending or vortexing to homogeneity, allowing particulates to settle, and retention of the supernatant; pulsification (for example for at least 30 seconds, at least 60 seconds, or at least 120 seconds); and/or coarse filtration (such as a with a material having a pore size of at least 100 μm, at least 200 μm, or at least 300 μm). These treatments can be performed before or after the photobleaching step.

One skilled in the art will appreciate that combinations of such centrifugation and filtration can be used. In some examples, such methods significantly reduce the amount of particulate in the sample that is not bacteria, such as autofluorescent food particles.

D. Addition of Agents to Detect the Target Bacteria

After photobleaching the sample, and separating the bacteria from the sample, reagents are added to the resulting isolated bacterial sample, which permit detection of the one or more target bacteria.

The isolated bacterial sample is incubated with one or more specific binding agents specific for the target bacterium, under conditions that permit the specific binding agent to bind to cell surface proteins of the target bacterium. If several target bacteria are to be detected, specific binding reagents can be used that are specific for each target bacterium. In some examples, a plurality of specific binding agents are used simultaneously, each associated with a different label (which emits light at a distinct wavelength, thus permitting detection of each specific binding agent-bacterium complex). For example, specific binding agent 1 specific for target bacterium 1 can be directly or indirectly labeled with a fluorophore that emits at wavelength 1 (such as about 525 nm), specific binding agent 2 specific for target bacterium 2 can be directly or indirectly labeled with a fluorophore that emits at wavelength 2 (such as about 575 nm), specific binding agent 3 specific for target bacterium 3 can be directly or indirectly labeled with a fluorophore that emits at wavelength 3 (such as about 610 nm), and so on. As each specific binding agent is associated with a particular label that is distinguishable from the labels on the specific binding reagents for other target bacteria, this permit detection of a plurality of target bacteria in the same sample, for example at the same time or contemporaneously. For example, if a signal at wavelength 1 is detected, this indicates that target bacterium 1 is present; if a signal at wavelength 2 is detected, this indicates that target bacterium 2 is present; if a signal at wavelength 3 is detect, this indicates that target bacterium 3 is present; and so on.

In some examples, the sample is also incubated with single or multiple detergents or surfactants, such as a mild detergent. Such incubation can be under conditions sufficient to substantially reduce the presence of particles that may interfere with the flow cytometric analysis, expose surface epitopes on the target bacteria, thereby permitting the target bacteria to specifically bind to the specific binding agent, or combinations thereof. For instance, such interfering particles may be fluorescent oil droplets that may be present in fatty foods, such as chicken, ice cream, peanut butter, and the like. If not eliminated, such particles may be mistaken for bacteria or other microbes during flow cytometry. In other embodiments, detergents may be used to suspend and/or stabilize the samples. Detergents suitable for use in the present disclosure can include without limitation and in various combinations, polyethylene glycol, EDTA, Triton-100®, Tween®-20, Tween®-80, sodium dodecyl sulfate (SDS), and the like. In addition, detergents may be present in a buffer and/or another solution at various concentration ranges. In some embodiments, such concentration ranges may vary from 0.01% by weight to 5% by weight of the solution. In other embodiments, such concentration ranges may vary from 0.1% by weight to 5% by weight of the solution, such as 1% by weight to 5% by weight, 1% by weight to 2% by weight, or 3% by weight to about 5% by weight of the solution. In various embodiments, a solution may include from about 0.1% by weight to about 5% by weight of Tween®-80 or Tween®-20.

In some embodiments, a high detergent concentration is used, such as about 3% to about 5% by weight. For example, the use of Tween®-80 at about 5% by weight of a buffered sample solution can stabilize the binding of antibodies to specific epitopes on a bacterial surface. Since detergents may also adversely affect the viability of bacteria after prolonged exposure, the sample treated with high concentrations of detergents are exposed for only short periods of time such as, for example, from 30 seconds to 30 minutes or 30 seconds to 5 minutes. In some examples, a sample may be initially treated with a low concentration (e.g., less than about 3% by weight) of a detergent for a sufficient period of time to provide for removal of interfering particles. Thereafter, the detergent concentration may be increased and the sample further mixed for a short period of time (e.g., 30 seconds to 5 minutes) before analysis.

In some examples, the isolated bacterial sample is contacted with an agent that permits a determination of whether the bacteria detected are live or dead. In one example, the isolated bacterial sample is incubated with an impermeable DNA-intercalating dye, such as propidium iodide. For example, the isolated bacterial sample can be incubated with such an agent for at least 3 minutes, at least 5 minutes, or at least 7 minutes, such as 5 to 7 minutes.

III. Methods of Detection

Exemplary means used to detect one or more target bacteria include specific binding agents, such as an antibody (or fragment thereof) or aptamer specific for a target bacterial cell, as well as DNA, RNA or peptide nucleic acid (PNA) probes specific for the target bacterium. Such specific binding agents can be obtained from a commercially available source or prepared using techniques common in the art. Such specific binding agents can be used in the methods provided herein.

Specific binding reagents include, for example, antibodies or functional fragments or recombinant derivatives thereof, aptamers, mirror-image aptamers, or engineered nonimmunoglobulin binding proteins based on any one or more of the following scaffolds: fibronectin (e.g., ADNECTINS™ or monobodies), CTLA-4 (e.g., EVIBODIES™), tendamistat (e.g., McConnell and Hoess, *J. Mol. Biol.*, 250:460-470, 1995), neocarzinostatin (e.g., Heyd et al., *Biochem.*, 42:5674-83, 2003), CBM4-2 (e.g., Cicortas-Gunnarsson et al., *Protein Eng. Des. Sel.*, 17:213-21, 2004), lipocalins (e.g., ANTICALINST™; Schlehuber and Skerra, Drug Discov. Today, 10.23-33, 2005), T-cell receptors (e.g., Chlewicki et al., *J. Mol. Biol.*, 346:223-39, 2005), protein A domain (e.g., AFFIBODIES™; Engfeldt et al., *ChemBioChem*, 6:1043-1050, 2005), Im9 (e.g., Bernath et al., *J. Mol. Biol.*, 345:1015-26, 2005), ankyrin repeat proteins (e.g., DARPins; Amstutz et al., *J. Biol. Chem.*, 280:24715-22, 2005), tetratricopeptide repeat proteins (e.g., Cortajarena et al., Protein Eng. Des. Sel., 17:399-409, 2004), zinc finger domains (e.g., Bianchi et al., *J. Mol. Biol.*, 247:154-60, 1995), pVIII (e.g., Petrenko et al., *Protein Eng.*, 15:943-50, 2002), GCN4 (Sia and Kim, *Proc. Natl. Acad. Sci. USA*, 100:9756-61, 2003), avian pancreatic polypeptide (APP) (e.g., Chin et al., *Bioorg. Med. Chem. Lett.*, 11:1501-5, 2001), WW domains, (e.g., Dalby et al., *Protein Sci.*, 9:2366-76, 2000), SH3 domains (e.g., Hiipakka et al., *J. Mol. Biol.*, 293:1097-106, 1999), SH2 domains (Malabarba et al., *Oncogene*, 20:5186-5194, 2001), PDZ domains (e.g., TELOBODIES™; Schneider et al., *Nat. Biotechnol.*, 17:170-5, 1999), TEM-1 β-lactamase (e.g., Legendre et al., *Protein Sci.*, 11:1506-18, 2002), green fluorescent protein (GFP) (e.g., Zeytun et al., Nat. Biotechnol., 22:601, 2004), thioredoxin (e.g., peptide aptamers; Lu et al., Biotechnol., 13:366-372, 1995), Staphylococcal nuclease (e.g., Norman, et al., *Science*, 285:591-5, 1999), PHD fingers (e.g., Kwan et al., *Structure*, 11:803-13, 2003), chymotrypsin inhibitor 2 (CI$_2$) (e.g., Karlsson et al., *Br. J. Cancer*, 91:1488-94, 2004), bovine pancreatic trypsin inhibitor (BPTI) (e.g., Roberts, *Proc. Natl. Acad. Sci. USA*, 89:2429-33, 1992) and many others (see review by Binz et al., *Nat. Biotechnol.*, 23(10):1257-68, 2005 and supplemental materials).

Specific binding reagents also'include antibodies. The term "antibody" refers to an immunoglobulin molecule (or combinations thereof) that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), single chain Fv antibodies (scFv), polypeptides that contain at least a portion of an immunoglobulin that is sufficient to confer specific antigen binding to the polypeptide, and antigen binding fragments of antibodies. Antibody fragments include proteolytic antibody fragments [such as F(ab')2 fragments, Fab' fragments, Fab'-SH fragments, Fab fragments, Fv, and rIgG], recombinant antibody fragments (such as sFv fragments, dsFv fragments, bispecific sFv fragments, bispecific dsFv fragments, diabodies, and triabodies), complementarity determining region (CDR) fragments, camelid antibodies (see, for example, U.S. Pat. Nos. 6,015,695; 6,005,079; 5,874,541; 5,840,526; 5,800,988; and 5,759,808), and antibodies produced by cartilaginous and bony fishes and isolated binding domains thereof (see, for example, International Patent Application No. WO03014161).

A Fab fragment is a monovalent fragment consisting of the VL, VH, CL and CH1 domains; a F(ab')$_2$ fragment is a bivalent fragment comprising two Fab fragments linked by a disulfide bridge at the hinge region; an Fd fragment consists of the VH and CHI domains; an Fv fragment consists of the VL and VH domains of a single arm of an antibody; and a dAb fragment consists of the VH domain (see, e.g., Ward et al., Nature 341:544-546, 1989). A single-chain antibody (scFv) is an antibody in which a VL and VH region are paired to form a monovalent molecule via a synthetic linker that enables them to be made as a single protein chain (see, e.g., Bird et al., *Science*, 242: 423-426, 1988; Huston et al., *Proc. Natl. Acad. Sci. USA*, 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., *Proc. Natl. Acad. Sci. USA*, 90:6444-6448, 1993; Poljak et al., *Structure*, 2:1121-1123, 1994). A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a "bispecific" or "bifunctional" antibody has two different binding sites.

In some examples, an antibody specifically binds to a target bacterium (e.g., an *E. coli* or *Salmonella*-specific antibody) with a binding constant that is at least $10^3$ M$^{-1}$ greater, $10^4$ M$^{-1}$ greater or $10^5$ M$^{-1}$ greater than a binding constant for other molecules in a sample. In some examples, a specific binding reagent (such as an antibody (e.g., monoclonal antibody) or fragments thereof) has an equilibrium constant (K$_d$) of 1 nM or less. For example, a specific binding agent may bind to a target bacteria with a binding affinity of at least about $0.1 \times 10^{-8}$M, at least about $0.3 \times 10^{-8}$M, at least about $0.5 \times 10^{-8}$M, at least about $0.75 \times 10^{-8}$ M, at least about $1.0 \times 10^{-8}$M, at least about $1.3 \times 10^{-8}$ M at least about $1.5 \times 10^{-8}$M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Methods of generating antibodies (such as monoclonal or polyclonal antibodies) are well established in the art (for example, see Harlow and Lane, *Antibodies: A Laboratory Manual*, Cold Spring Harbor Laboratory, New York, 1988). For example peptide fragments of a target bacterium can be conjugated to carrier molecules (or nucleic acids encoding such epitopes or conjugated RDPs) can be injected into non-human mammals (such as mice or rabbits), followed by boost injections, to produce an antibody response. Serum isolated from immunized animals may be isolated for the polyclonal antibodies contained therein, or spleens from immunized animals may be used for the production of hybridomas and monoclonal antibodies. In some examples, antibodies are purified before use.

In one example, monoclonal antibody to a target bacterium, can be prepared from murine hybridomas according to the classical method of Kohler and Milstein (*Nature*, 256:495, 1975) or derivative methods thereof. Briefly, a mouse (such as Balb/c) is repetitively inoculated with a few micrograms of the selected peptide fragment from the target bacterium on carrier conjugate thereof over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.*, 70:419, 1980), and derivative methods thereof. Selected positive clones can be expanded and their monoclonal antibody product harvested for use.

Commercial sources of antibodies include Santa Cruz Biotechnology, Inc. (Santa Cruz, Calif.), Sigma-Aldrich (St. Louis, Mo.), and Abcam (Cambridge, UK). Table 1 shows exemplary commercial sources of antibodies for exemplary target bacterium.

TABLE 1

Exemplary commercial sources of antibodies.

| | Antibody type | Source | Catalog # |
|---|---|---|---|
| *E. coli* O157 | | Kirkegaard & Perry Laboratories, Inc. | 01-95-90-MG |
| | Polyclonal | Abcam | ab30521 |
| | Monoclonal | MyBioSource | MBS312801 |
| *Campylobacter jejuni* | Monoclonal | Santa Cruz Biotechnology, Inc. | sc-58099 and sc-58100 |
| | Polyclonal | Abcam | ab22542 |
| *Salmonella* | Polyclonal | Abcam | ab35156 |
| | Monclonal | Abcam | ab72989 |
| *Listeria monocytogenes* | Polyclonal | Thermo Scientific | PA1-7230 |
| | Monoclonal | Santa Cruz Biotechnology, Inc. | sc-52057 |
| | Monoclonal | Novus Biologicals | LX32 |

Disclosed specific binding agents also include aptamers specific for a target bacterium. In one example, an aptamer is a single-stranded nucleic acid molecule (such as, DNA or RNA) that assumes a specific, sequence-dependent shape and binds to a target bacterium with high affinity and specificity. Aptamers generally comprise fewer than 100 nucleotides, fewer than 75 nucleotides, or fewer than 50 nucleotides (such as 10 to 95 nucleotides, 25 to 80 nucleotides, 30 to 75 nucleotides, or 25 to 50 nucleotides). In a specific embodiment, disclosed specific binding reagents are mirror-image aptamers (also called a SPIEGELMERT™). Mirror-image aptamers are high-affinity L-enantiomeric nucleic acids (for example, L-ribose or L-2'-deoxyribose units) that display high resistance to enzymatic degradation compared with D-oligonucleotides (such as, aptamers). The target binding properties of aptamers and mirror-image aptamers are designed by an in vitro-selection process starting from a random pool of oligonucleotides, as described for example, in Wlotzka et al., *Proc. Natl. Acad. Sci.* 99(13):8898-8902, 2002. Methods of generating aptamers are known in the art (see e.g., Fitzwater and Polisky (*Methods Enzymol.*, 267:275-301, 1996; Murphy et al., *Nucl. Acids Res.* 31:e110, 2003) and include the whole bacterium-based SELEX procedure. Aptamers specific for a particular bacterium are known in the art, such as those specific for *S. aureus* (see Cao et al., *Nuc. Acids Res.* 37:4621-8, 2009), *L. acidophilus* (see Hamula et al., *Anal. Chem.* 80:7812-9, 2008), and *E. coli* (Lee et al., *Biosens. Bioelectron.* 15:3550-5, 2009), *E. coli* $O_{157}$:H7 (see Lee et al., *Biochem. Biophys. Res. Comm.* 417:414-20, 2012 and Wu et al., *PLoS One* 7::e48999, 2012,), *Salmonella* (e.g., see Joshi et al., *Mol. Cell. Probes* 23:20-8, 2009). and *S. enterica serovar Typhi* (Pan et al., *Antimicrob. Agents Chemother.* 49:4052-60, 2005). Such aptamers can include a label, such as a fluorescent label, to permit their detection.

In another example, an aptamer is a peptide aptamer that binds to a target bacterial protein with high affinity and specificity. Peptide aptamers include a peptide loop (e.g., which is specific for the target bacterial protein) attached at both ends to a protein scaffold. This double structural constraint greatly increases the binding affinity of the peptide aptamer to levels comparable to an antibody's (nanomolar range). The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

Disclosed specific binding agents also include peptide nucleic acids (PNAs) specific for a target bacterium. PNAs specific for bacteria are commercially available, for example from bioMérieux, Inc. (Durham, N.C.).

Specific binding agents optionally can be directly labeled with a detectable moiety. Useful detection agents include fluorescent compounds (including fluorescein, fluorescein isothiocyanate, rhodamine, 5-dimethylamine-1-napthalene-sulfonyl chloride, phycoerythrin, lanthanide phosphors, or the cyanine family of dyes (such as Cy-3 or Cy-5) and the like); bioluminescent compounds (such as luciferase, green fluorescent protein (GFP), or yellow fluorescent protein); enzymes that can produce a detectable reaction product (such as horseradish peroxidase, β-galactosidase, luciferase, alkaline phosphatase, or glucose oxidase and the like), or radiolabels (such as $^3$H, $^{14}$C, $^{15}$N, $^{35}$S, $^{90}$Y, $^{99}$Tc, $^{111}$In, $^{125}$I, or $^{131}$I). In other examples, specific binding agents are indirectly labeled, for example by use of a secondary agent that includes a detectable moiety (such as a fluorescently-labeled secondary antibody).

Thus, in some examples the target bacteria are detected by detecting a label associated with the specific binding agent. For example, when the specific binding agent binds to its target bacterium, it generates a specific binding agent-target bacteria complex, which can be detected by a label associated directly or indirectly with the specific binding agent. In some examples, the label emits light at a wavelength of at least 490 nm, such as at least 500 nm, at least 550 nm, at least 600 nm, or at least 650 nm, such as 490 to 700 nm. This light emitted, which is specific for a particular label, can be detected and indicate the presence of a particular bacterium. Such signals can be detected using know methods, such as flow cytometry or fluorescence microscopy.

Immunohistochemistry (IHC) is an exemplary technique useful for detecting target bacteria using the disclosed methods. Flow cytometry and microscopy can be used in such methods. Thus, in some examples the method includes introducing the sample into a flow cytometer. Antibodies (e.g., monoclonal and/or polyclonal antibodies) specific for a target bacteria can be used to detect the presence of the target bacteria in a test sample. The antibodies can be detected by direct labeling of the antibodies themselves, for example, with fluorescent labels, hapten labels such as, biotin, or an enzyme such as horseradish peroxidase or alkaline phosphatase. Alternatively, unlabeled primary antibody specific for the target bacteria is used in conjunction with a labeled secondary antibody, comprising antisera, polyclonal antisera or a monoclonal antibody specific for the primary antibody.

In some examples not only are target bacteria detected, but a determination is made as to whether the detected bacterium is live or dead. For example, the bacteria can be contacted with an agent impermeable to live cells, but can permeate dead cells, such as propidium iodide (PI), Hoechst dyes, or ethidium bromide. Thus, when PI is detected (for example by detecting light having a wavelength of about >670 nm), this indicates that the detected bacterium is dead, while the absence of detected PI indicates that the detected bacterium is live.

In some examples when flow cytometry is used, the sample analyzed is gated to further exclude non-bacterial particulates. Examples of such methods can be found in PCT/US09/54071 and US Publication No. 20110217694 (both herein incorporated by reference). For example, the flow cytometer can be optimized by a) increasing a sensitivity of at least one detection channel on the flow cytometer by increasing a gain on the at least one detection channel; b) assigning a signal threshold value for each at least one detection channel; and c) collecting raw data from the flow cytometer for a time range. The time range includes a plurality of intervals. The raw data includes signals and non-signals for each of the at least one detection channels. The optimization can include d) analyzing the raw data from each of the plurality of intervals to provide processed data. Analyzing includes eliminating raw data from each of the plurality of intervals in which the signals do not exceed the assigned signal threshold for each at least one detection channel and selecting raw data from each of the plurality of intervals in which the signals do exceed the assigned signal threshold for each at least one detection channel. In a specific example, 2D gates are determined empirically, by growing target isolates under standard conditions and configuring the gates so that they enclose various isolates of the target bacterium. This makes each gate as small as possible for inclusivity and thus maximizes the exclusion of random non-target signals.

In some examples, the sample is analyzed with fluorescence microscopy or flow cytometry to detect labels associated with the specific-binding agent-target bacterium complexes. Thus, the disclosed methods can include introducing the specific-binding agent-target bacterium complexes into a flow cytometer or onto a microscope slide and analyzing the sample to detect specific-binding agent-target bacterium complexes. The specific-binding agent-target bacterium complexes include at least one label. The step of detecting the one or more target bacteria thus can include exciting the sample (such as an isolated bacterial sample that may contain labeled specific-binding agent-target bacterium complexes) by at least one light source and detecting at least one fluorescent emission wavelength. The light source used to excite the label and the filter used to detect the label can depend on the particular label or fluorophore used. Exemplary light sources include, ultraviolet light, violet light, xenon light, blue light, near infrared light, visible light (e.g., yellow or green), and combinations thereof. In one example, the light source is a laser. Exemplary fluorescent emission wavelengths include those in the range of about 380 nm to about 760 nm, such as about 400 to 700 nm, for example 525, 575, 610, and 675 nm.

IV. Exemplary Bacteria Detected

The disclosed methods permit detection of bacteria, such as those present in a sample. In some examples, the method permits detection of at least two different types of bacteria (such as at least 3, at least 4, at least 5, or at least 6 different types of bacteria, such as 2, 3, 4, 5, 6, 7, 8, 9 or 10 different types of bacteria), for example contemporaneously or simultaneously (e.g., in the same sample or in the same reaction vessel). For example, samples obtained from a human or veterinary subject can be screened to determine if the subject has a bacterial infection. In addition, food samples can be screened to determine if they are contaminated with bacteria. For example, food can become contaminated with one or more bacteria during growing, harvesting, processing, storing, shipping, or final preparation. Furthermore, environmental samples can be screened to determine if they are contaminated with bacteria. For example, samples obtained by swabbing a surface (such as a surface used in food processing, storage, and the like) can be screened to determine if they are contaminated with bacteria.

In some examples, the methods permit detection of the bacteria, even when there are only a few bacteria present in the sample (such as no more than 100, no more than 75, no more than 50, no more than 25, no more than 20, no more than 10, no more than 5, no more than 4, no more than 3, no more than 2, such as 1-100, 1-75, 1-50, 1-25, 1-20, 1-10, 1-5, 5-100, 5-75, 5-50, or 1, 2, 3, 4, 5, 6, 7, 8, 9, or 10 bacteria present in the sample). However, one skilled in the art will appreciate that the methods can also be used when there are many bacteria in the sample (such as at least 100 bacteria, such as at least 500, at least 1000, or at least 10,000 bacteria). In a specific example, the methods permit detection of a single bacterium present in a sample.

Bacteria can be classified as gram-negative or gram-positive. Exemplary gram-negative bacteria include, but are not limited to: *Escherichia coli* (e.g., strains K-12, O157, and O157:H7), *Shigella* spp. (such as *S. dysenteriae*), *Salmonella* spp. (e.g., *S. typhimurium*), *Campylobacter jejuni* and *Vibrio cholera* (e.g., strains O1 and non-O1). Exemplary gram-positive bacteria include, but are not limited to: *Bacillus* spp. (e.g., *B. anthracis* and *Bacillus cereus*), *Clostridium* spp. (e.g., *C. perfringens* and *C. botulinum*), *Staphylococcus aureus* (such as Methicillin-resistant *S. aureus* (MRSA), *Streptococcus* spp., *Pseudomonas*, and *Neisseria gonorrhoeae*. Other exemplary bacteria that can be detected with the disclosed methods include, but are not limited to: *Listeria monocytogenes, Staphylococcal enteritis, Vibrio parahaemolyticus, Vibrio vulnificus, Yersinia enterocolitica, Yersinia pseudotuberculosis, Brucella* spp., *Corynebacterium ulcerans, Coxiella burnetii, Plesiomonas shigelloides, Pseudoalteromonas tetraodonis, Mycobacterium tuberculosis, Bordetella pertussis, Francisella tularensis, Helicobacter pylori*, and *Borrelia burgdorferi*. In one example the target bacterium is an agricultural pest, such as *Clavibacter michiganensis* subspecies *michiganensis* (Cmm).

V. Outputs

In some embodiments, once a sample is analyzed, an indication of that analysis can be displayed and/or conveyed to a user. For example, the results of the test can be provided to a user (such as a clinician or other health care worker, laboratory personnel, or patient) in a perceivable output that provides information about the results of the test. In some embodiments, the output is a paper output (for example, a written or printed output), a display on a screen, a graphical output (for example, a graph, chart, voltammetric trace, or other diagram), or an audible output.

In other embodiments, the output is a diagnosis, such as whether the sample analyzed contains the target bacterium or not. In additional embodiments, the output is a graphical representation, for example, a graph or dot plot that indicates the value (such as amount or relative amount) of the number of target bacteria present in the sample. In some examples, the output is a number on a screen/digital display indicating the probability that the sample contains the target bacteria. In some examples, the output is text, indicating whether or not the sample contains the target bacteria along with corresponding implications. Sensitivity, specificity, and confidence intervals may also be a part of the output. These outputs can be in the form of graphs or tabulated numbers. In some embodiments, the output is communicated to the user, for example by providing an output via physical, audible, or electronic means (for example by mail, telephone, facsimile transmission, email, or communication to an electronic record).

In some embodiments, the output is accompanied by guidelines for interpreting the data, for example, numerical or other limits that indicate whether the test sample is contaminated or infected with one or more target bacteria. The indicia in the output can, for example, include normal or abnormal ranges or a cutoff, which the recipient of the output may then use to interpret the results, for example, to arrive at a diagnosis, prognosis, or treatment plan. In other embodiments, the output can provide a recommended therapeutic regimen. In some embodiments, the test may include determination of other clinical information (such as determining the amount of one or more additional biomarkers in the sample).

Example 1

Materials and Methods

This example describes the materials and methods used to generate the results described in Examples 2-5.
Instrumentation and Method Overview The flow cytometer was a model 9013 (LITMUS RAPID-B, North Little Rock, Ark.), with 130 nm resolution useful in detecting bacteria (Steen, 2000). *E. coli* serotype O157:H7 isolates, either American Type Culture Collection (ATCC) No. 43888, which does not produce Shiga-like toxin I or II, ATCC 43895, which produces both Shiga-like toxins I and II, or ATCC 43888, which lacks the toxin genes, were used as targets.

Figure 1:
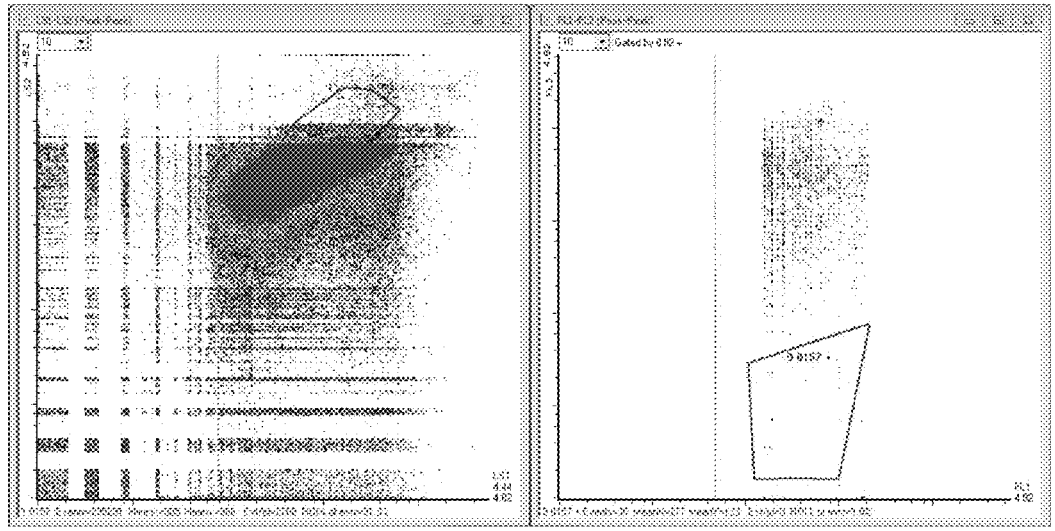
FIG. 1 shows two dot plot screens from a blank spinach sample analyzed for *E. coli* O157 using the original RAPID-B method after a 5 µm filtration alone. The dots in the 2D light scatter display on the left represent the large number of particles from background microflora or spinach cellular organelles and debris. The image on the right shows thirty detected fluorescent events inside the quadrilateral gate which were not target *E. coli* O157 cells since the sample was a blank.
Figure 2:
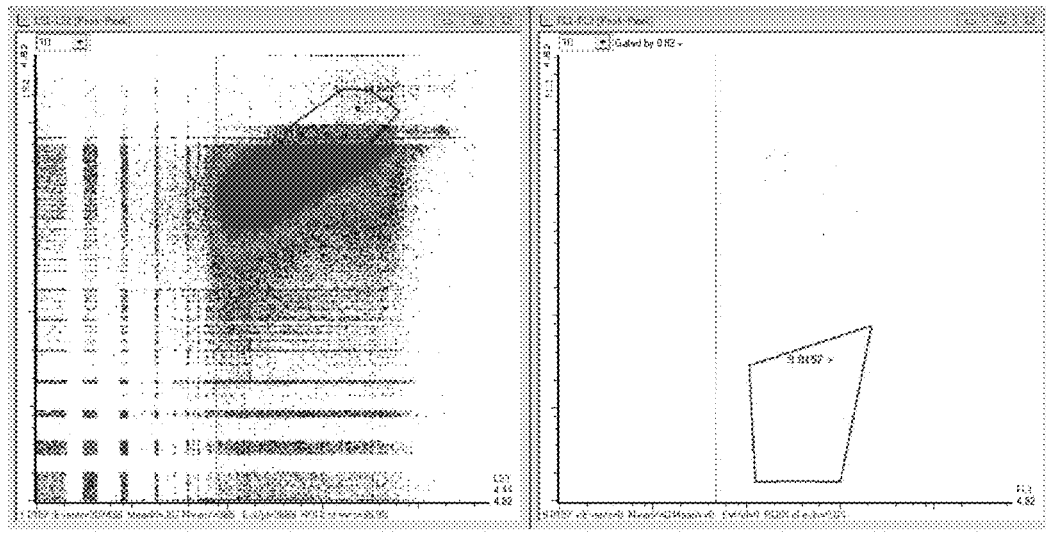
FIG. 2 shows two dot plot screens from a 5-µm filtered spinach blank treated with phloxine B sensitizer and light using the disclosed improved methods. The dot pattern in the 2D light scatter display on the left signifies the large number of particles arising from background microflora or spinach cellular organelles and debris. The image on the right shows that photobleaching destroyed most autofluorescence in particles, including all producing events inside the quadrilateral counting gate.
Figure 3:
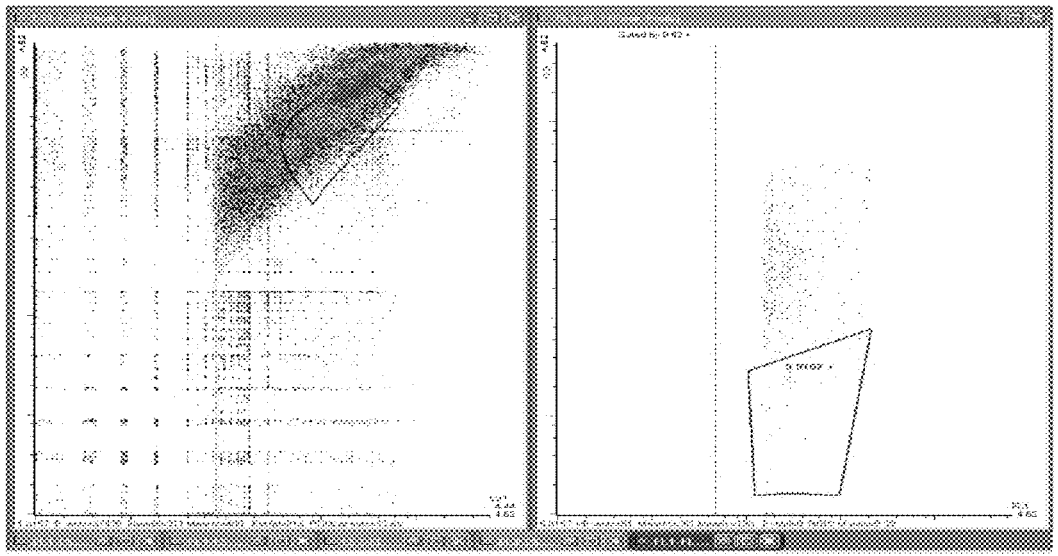
FIG. 3 shows typical analysis of a 5-µm filtered spinach blank using *E. coli* O157 RAPID-B reagents followed by Percoll gradient centrifugation alone (no photobleaching step).

Samples were prepared by the addition of two reagents (Vivione Biosciences, Little Rock, Ark.). Reagent A contains FL1 fluorophore-labeled polyclonal antibodies that bind to cell surface epitopes uniquely associated with *E. coli* O157. Reagent B contains ingredients that prepare the bacterial cells so that surface epitopes are accessible. Reagents were allowed to incubate at room temperature with the samples for six minutes. The sample was then run on the instrument and results were displayed in real time as two dimensional dot plots. FIGS. 1-3 show initial and final dot plots and their respective gates for the *E. coli* O157 method used on spinach sample blanks. Each dot inside the final gate represented an event that successfully passed a series of prior gates. Each dot represents one particle exhibiting the particular combination of light scatter and fluorescence properties associated with a fluorescence-tagged target cell.

Sample analysis required no further processing. The final fluorescence selection gate was a small quadrilateral. The number of dots that fell within the quadrilateral presumptively represent live cells of the target bacterium, *E. coli* O157.

Analysis of a negative sample requires no further processing. For presumptive positives, FDA regulatory requirements require confirmation and isolation of the causative agent, which can be accomplished using the sample's unused (non-photobleached) enrichment medium. In the last external laboratory study, some enrichment residuals were reanalyzed by RAPID-B after approximately 24 hours to confirm or correct results.
Threshold Definition, Counts-to-Threshold Ratio, Limit of Detection and Time-to-Results The standard metric, signal-to-noise ratio (SN), allows analysts to distinguish a true signal (S) from noise (N) based on signal intensity relative to random variations. However, after RAPID-B signal processing using the designated gates, a signal either is or is not a qualifying event and random variation s zero, N=0. To avoid dividing by zero, a new metric is provided, the counts-to-threshold ratio (C/T), in which the denominator, "threshold," is always positive (Buzatu et al., 2011; Wilkes et al., 2012). In evaluating an unknown sample, any count (C) greater than threshold (T) is presumed positive for the target pathogen. Based on a definition of T as the average of method blank sample counts plus three standard deviations in that average, if C/T>1.0 for an assay, the result has a >99% probability of being a true positive (Wilkes et al., 2012).

Several factors affect the method LOD and TTR for target cell analysis of foods, such as i) food type, age, and condition—because that affects background and therefore threshold (T); ii) target cell number (affects C); iii) sample size collected (affects C and T); iv) recovery efficiency plus concentration during sample preparation (affects C); v) volume analyzed on the instrument (affects C); and vi) the quality of sample handling during method execution (affects C and T). If enrichment is used, additional factors can include: vii) lag-phase duration (affects C, controlled by refrigeration temperature shock and change in nutrients—i.e., carbon source); viii) cell-division rate (affects C); and ix) growth-period duration (affects C and T).

The method LOD was determined by spiking increasingly lower numbers of target *E. coli* O157:H7 (ATCC 43895), varying from ca. 140 down to 1, into a large volume (450 ml) of brain heart infusion (BHI) liquid culture medium. Immediately after inoculation, the medium was stirred vigorously and split into six equal aliquots of 75 ml. (A slightly different method was used for spiking samples in the FERN Level 2 and the very low level test described below). For two of the method LOD experiments, the bulk spiking and aliquot subdivisions were repeated so that twelve replicates were available to strengthen quantitative inferences. Each aliquot was poured into a 710 ml Whirl-pak filter bag containing a 25 g sample of locally purchased, within its "best if used by" date, bagged raw spinach. Analysis then proceeded with step 4 of the improved method (see Example 1 Improved RAPID-B method, standard operating procedure). The large volume spiking levels, confirmed later by triplicate TSA plate count assays of the various inoculum suspensions, averaged 140±17.4, 80±4.1, 26.3±17.0, 4.0±3.6, 0.7±0.6, and 0.3±0.7 cells, respectively. After extended growth of medium left over at step 7 (see Example 1 Improved RAPID-B method, standard operating procedure), samples reporting negative results by RAPID-B were reanalyzed by RAPID-B to determine whether they had actually contained any *E. coli* O157 cells. Method breakdown level—failure to detect target contamination—would be based on the fraction of aliquots at an inoculation level confirmed as true positives but RAPID-B false negatives after the 5 hour growth. Results are reported in Table 3, discussed in Example 3.
Spiking and Culture Confirmation Procedure Spiking of bacteria on spinach leaves used suspensions of *E. coli* cells, ser. O157:H7 (ATCC 43888) for the analyte and/or a non-serotype O157 strain *E. coli* (ATCC 35421), the latter for competitive response assessment (details below). It was independently confirmed that *E. coli* (ATCC 35421) was not cross-reactive for the antibodies used by RAPID-B to detect the target *E. coli* O157.

Cells were grown to stationary phase in trypticase soy broth (TSB) and then diluted to $10^{-5}$ and $10^{-6}$ in sterile phosphate-buffered saline (PBS). Growth of cells in TSB before their use as an inoculum was specified to simulate stress of incurred contaminants in spinach, which would be required during enrichment to adjust from a food like spinach to BHI (i.e., a different carbon source).

For the *E. coli* target bacteria, the cells were counted and suspensions were carefully diluted using sterile PBS to create working suspensions with approximately 1500 or 150 cells per ml. After vortexing vigorously to homogeneity, 100 µl of the appropriate working suspension was used to spike each high positive (ca. 150 cells) or low positive (ca. 15 cells) spinach sample; 100 µl of sterile PBS (0 cells) was applied to control spinach samples. Competitor bacteria spiking was accomplished similarly: the spiking level was 75 cells. To confirm *E. coli* O157:1-17 (ATCC 43888) and non-O157 *E. coli* (ATCC 35421) spiking levels, TSA plates were inoculated at the time of spinach spiking with a 100 µL, aliquot of the spiking suspension. CFUs were counted after overnight growth at 37.5° C.

After spiking onto spinach, and rubbing the suspensions onto leaves, samples were aged by overnight refrigeration at 5° C. That is, cells spiked onto the spinach were then cold-stressed. This was to mimic the experience of bacteria in perishable food samples sent under refrigeration for analysis by an outside laboratory. By this experimental design, results obtained for the RAPID-B assay would not exaggerate system performance but produce a reasonable estimate of both TTR and LOD.

Validation Design

A FERN Level 2 Independent Lab validation (McGrath, 2006) was also determined. After sample handling and growth details were specified as a standard operating procedure, overall method performance was assessed by personnel from an independent laboratory, FDA's Arkansas Regional Laboratory (ARL), whose microbiologists executed both the RAPID-B and BAM 4a *E. coli* O157:H7 analyses.

The BAM method specifies an initial growth step at 37.5° C. using enterohemorrhagic *E. coli* (EHEC) enrichment broth—TSB modified after 5 hours by addition of selective growth inhibitors, BAM Medium 156 (Weagant et al., 1995). The corresponding RAPID-B method uses BHI at 42° C. without selective growth inhibitors. Because of the different growth media and conditions, parallel rather than split samples were used.

A third lab prepared spiked samples (samples where bacteria were added at known amounts) and assured a double blind study design. FERN 2 validation requires a minimum of two inoculation levels and six replicates at each level. This design used three levels: 6 blank samples inoculated with sterile PBS blanks, 6 low positive samples (about 15 target cells), and 6 high positive samples (about 122 target cells). Together the BAM and RAPID-B sample panel comprised 2×(6+6+6)=36 plus 4 more, a total of 40 samples. The 4 extra samples specified addition of a competitive microorganism, discussed below.

Inoculations during validation studies were made by rubbing cell suspensions into 25 g spinach samples, rather than by pouring 75 ml cell suspensions in BHI onto the samples, as was done for the LOD determination FERN Level 2 validation typically includes an assessment of method ruggedness in the presence of an excess of competitive, non-target microflora similar to the target cells. The spinach samples used were not sterile so the presence of competitive bacteria (ca. $10^6$ per sample) was assured, but their competitive potential (metabolic similarity to *E. coli*) was unknown. To address the competitive microflora specification, the target *E. coli* O157 strain spiked at ca. 15 cells per 25 g of spinach was augmented by addition of ca. 75 cells non-O157 *E. coli* (ATCC 35421) (results below, Table 4, the experiment labeled "Low (Comp)", meaning inoculation of low level target cells plus the competitor. This experiment comprised two samples, one each for RAPID-B and BAM.

Two additional samples were spiked with the non-O157 *E. coli* (ATCC 35421) alone at the 75 cell level, rows labeled "Blank (Comp.)," meaning sample blank with only competitor added. The average spiking levels were confirmed by plate media count for the low level, high level *E. coli* O157:H7 and the non-O157 *E. coli* (ATCC 35421) competitor: 15, 122, and 70, respectively.

TSB rather than BHI was specified for growing inoculum suspensions (i.e., the cells were grown in a medium different from the one used for their recovery) and after inoculation the raw spinach leaves were aged overnight at 5° C. (see above). These modifications are not required for FERN Level 2 validation but can help address any concerns that rapid system performance was exaggerated.

BAM 4a Procedure—Preparation of Spinach Samples

Reference method samples were prepared by spiking with the same working suspensions and procedures used in the first three steps of the RAPID-B method (see below Improved RAPID-B method, standard operating procedure). Each sample was subsequently processed using BAM 4a analytical procedures including real-time PCR and conventional isolation of presumptive positives (Feng et al., 2011).

Original RAPID-B Method—Preparation and Analysis of Spinach Samples

Spinach samples were processed as follows. This original method, which gave less than optimal results, used the following 12 steps. (1) 36 samples of fresh spinach, 25 g each, were weighed out to the nearest gram and placed into 710 ml Whirl-pak filter bags (Nasco, Fort Atkinson, Wis.). (2) 100 µl of PBS (Fisher, BP-399-1, diluted 10×) containing *E. coli* O157 cells at the appropriate low or high level was added to each sample (100 µl of sterile PBS was added to blanks). (3) The spiking or blank solutions were rubbed into the leaves through the plastic bag and sample bags were refrigerator-aged overnight. (4) The next day, 75 ml of Brain Heart Infusion medium, pre-warmed to 42° C., was added to each sample bag. (5) All samples were then incubated at 42° C. for 4 h. (6) After incubation, the bags were vortexed briefly to resuspend bacteria and 15 ml of each 75 ml sample was pipetted into a 15-ml centrifuge tube. The samples were then centrifuged in a batch at 11,200×g for 5 min. (7) 14.4 ml of the supernatant was decanted carefully, so the pellet at the bottom of the tube was not disturbed. (8) The pellet and remaining media were then briefly vortexed to resuspend cells. The 0.6 ml of suspension was transferred to a 1.5-ml microcentrifuge tube. (9) 0.9 ml of PBS was added to each 0.6-ml sample to bring the volume to 1.5 ml. The samples were then briefly vortexed to homogeneity. (10) Using an Eppendorf model 5415D centrifuge (Fisher Scientific, Pittsburgh, Pa.), the tubes were centrifuged in a batch at 11,200×g for 5 min to pellet the cells. (11) 1.4 ml of the supernatant was decanted and approximately 900 µl of PBS was added to bring the sample volume to 1.0 ml. Each sample was filtered through its own 25 mm, 5 PVDF syringe filter into a new 1.5-ml microcentrifuge tube. Air was blown through the filter to remove any remaining cell suspension. (12) 240 µl of RAPID-B Reagent B and 10 µl of Reagent A were added to each sample. The samples were then incubated at room temperature while vortexing lightly (25% setting on a Vortex Genie 2, Daigger) for 5 min.

This original procedure used 4 hour enrichment and produced results for non-spiked blanks (Example 2) that were frequently incorrect. False positive results by the first RAPID-B method for some blank samples could be attributed to autofluorescent spinach particles. The release of these particles was accentuated by the physical manipulation of the spinach leaves occurring when the inoculum was rubbed onto the surface of the leaves.

Procedure Improvements

Several strategies were employed to increase the C/T ratio. Cell counts were increased by lengthening incubation from 4 hours to 5 hours (or on follow-up testing to 6 hours), improving recovery, and increasing the volume sampled from 15 ml (as used in the original protocol) to 42.5 ml. The threshold (T) was decreased by (a) photobleaching the sample so that events qualified by particle-light-scatter would not pass through fluorescence gates and (b) physically separating bacteria from the enrichment matrix.

To increase recovery of *E. coli* O157:H7 cells adhering to spinach particles, 10 ml of sterile 0.1% TWEEN 20 detergent was added to each sample prior to the pulsification step. The 5 micron pore size filtration step was executed immediately prior to gradient centrifugation to separate target bacteria physically from the majority (~98%) of spinach particles.

Reducing or eliminating fluorescence of spinach particles proved difficult. It was hypothesized that autofluorescence might be extinguished or significantly reduced by chemical bleaching. Wilkes et al. (2012) showed that chlorine bleach reduced autofluorescence but also lysed target cells, preventing detection by flow cytometry. Oxygen bleach left target cells intact but immediately disrupted bacterial cell membranes and invalidated the viability assessment feature of the RAPID-B assay.

After incubation but before target cell tagging, a non-chemically reactive and non-toxic photo-sensitizing agent, phloxine B, was added to each sample. When exposed to intense light, it increases photobleaching (Foote, 1971). Singlet oxygen from phloxine B generated during light exposure reacts with the conjugated $\pi$ orbitals in autofluorescent compounds. Free radicals, such as singlet oxygen, interrupt conjugated systems by Diels-Alder type reactions either in a $2+2\pi$ orbital or a $2+4\pi$ orbital (Foote, 1971). These orbitals determine the light absorption and fluorescence character of organic molecules.

Sensitized exposure to photons allowed precise control of matrix bleaching, based on the intensity and duration of exposure and the concentration of phloxine B. It proved possible to photobleach the samples without rupturing bacterial cell membranes.

No aging of samples is required under FERN Level 2, but samples were refrigerated after inoculation onto the spinach. Inoculations during the validation study were made by rubbing cell suspensions into 25 g spinach samples rather than by pouring 75 ml cell suspensions in BHI onto the samples, as was done for the LOD determination.

The RAPID-B method stipulated an "uncertain results" criterion: it specified a 2 hour extended growth with reanalysis in any case in which the number of cells counted at the end of the initial 5 hour enrichment period was between 2× and 8× the average background of spinach blanks.

According to FERN Level 2 validation specifications, the low spiking level should be that at which the rapid method begins to experience fractional recovery (sporadic false negatives). Because RAPID-B had been shown to be more sensitive than BAM methods for some foods (Owens et al., 2009), modification of this criterion was considered to specify for the low level that for which either method experienced fractional recovery. The results reported below in Example 4 were from experiments in which the modified criterion would have been applied. As events transpired, neither method experienced fractional recovery when the low level inoculation was 14 cells, so the uncertain results criterion was irrelevant. But the validation did not meet the FERN Level 2 validation fractional recovery criterion.

It was desirable to do additional testing at a much lower target cell inoculation level. This presented a challenge because multiple tests have shown that the RAPID-B system can be more sensitive than reference methods (Owens et al., 2009). In this situation, concordance with reference method results would not be the appropriate metric. Fortunately, this situation was anticipated.

A 2006 AOACI contract study reported to FDA recommendations of a presidential task force on best practices in microbiological methodology (AOACI, 2006). The report specified alternative procedures when comparison to reference was impractical, particularly once rapid methods were developed that exceeded gold standard assays in sensitivity:

"Where applicable, the use of an established reference method is recognized as a preferred means to confirm the results of an alternative method. More recently, however, it has become increasingly apparent that, in some circumstances, the alternative method may be more sensitive than the traditional reference method(s) which are available for confirmation. In such instances it is the opinion of the Working Group that it is appropriate to employ alternative methodology to resolve discrepant results . . . . Possible approaches could include re-assay of discrepant samples . . . to confirm the validity of the preliminary determinations . . . . Another attractive alternative is the limit of detection validation . . . , as it eliminates the mandatory use of a reference method."

AOACI, 2006, pp 19, 20

The RAPID-B method LOD experiments reported in Example 3 and very low level tests with reanalysis reported in Example 5 embodied two of the suggested alternative validation strategies. The method LOD determination experimental design was described above (Threshold definition, counts-to-threshold ratio, limit of detection and time-to-results).

The follow-up test was designed to meet the fractional recovery criterion without requiring parallel BAM analyses. Unlike the LOD experiments, it also explored RAPID-B method detection sensitivity and ruggedness in the hands of non-expert users. Slight experimental design changes are detailed below (Improved RAPID-B method, follow-up validation, very low level target cell numbers). Results for the follow-up validation are summarized in Example 5.

Improved RAPID-B Procedure—Preparation and Analysis of Samples

The improved method used the following 22 steps.

(1) 40 samples of fresh spinach, 25 g each, were weighed and placed into 710 ml Whirl-pak filter bags (Nasco, Fort Atkinson, Wis.). (2) 100 µl of phosphate buffered saline was added to each sample. Depending on sample type, these contained either: 121.5±11.5 *E. coli* O157 ATCC 43888 cells (high level, 6 replicates each and low level (14±2.5), 6 replicates each for BAM 4a and RAPID-B); or no cells (blank, 6 replicates each); or 14±2.5 *E. coli* O157 and 70±2.5 non-O157 *E. coli* cells (ATTC 35421); (competitive assay, 6 replicates each); or 70±2.5 non-0157 *E. coli* cells (competitive assay blank, 1 sample each).

(3) The spike suspensions or blank solutions were rubbed into the leaves through each plastic bag and samples were refrigerator-aged overnight. (4) The next day, 75 ml of sterile, preheated (42° C.) BHI broth was added to each RAPID-B sample. BAM 4a samples were handled per the approved regulatory method. (5) 10 ml of 0.1% (v/v) TWEEN 20 in sterile water was added to each bag and gently swirled; bags were resealed.

(6) To liberate target cells into the surrounding medium, each sample was pulsified (Pulsifier model PUL 100, Microbiology International, Frederick, Md.) for 1 min. Bags were placed in an incubator at 42° C. (7) After a 5 hour incubation at 42° C., each sample bag was agitated to suspend bacteria and 42.5 ml of broth was transferred from the filtered volume of the Whirl-pak bag into a 50 ml sterile polypropylene centrifuge tube. (The remainder was saved for confirmation.). (8) 12.5 µl of a 0.01% phloxine B aqueous solution was added to each sample. (9) Samples were placed 30.5 cm from a 250 Watt halogen lamp with 115 V applied, inside a Vivione BioSciences Model 100 Photobleacher. Light intensity was measured as 43,000 lux; samples were exposed in batches of six for 1 min. (Concentrations, dimensions and intensities were empirically optimized.)

(10) Samples were centrifuged at 15,317×g for 20 min in a Beckman-Coulter Allegra 25 centrifuge fitted with a TA-10-250 rotor and 50 ml centrifuge tube inserts. (11) The supernatant was discarded to a biohazard container, which left approximately 100 µl of residual BHI and a pellet. (12) 1.2 ml of PBS was added to the remaining pellet; the mixture was re-suspended by vortexing. (13) The liquid was filtered through a 5 µm pore size syringe filter onto 600 µl of 60% Percoll (GE Healthcare Lifesciences,) in 1× phosphate buffered saline (PBS, Fisher, product BP-399-1), (Lindqvist, 1997) in a 2.0 ml microcentrifuge tube while maintaining the separation of the layers.

(14) Using an Eppendorf model 5415D centrifuge (Fisher Scientific, Pittsburgh, Pa.), the tubes were centrifuged at 16,100×g for 1 min. (15) Without disturbing the liquid in the bottom of each microcentrifuge tube, approximately 1.4 ml was pipetted off and discarded. This separated spinach particles from target bacteria, the latter remaining in the bottom 100-200 µl of liquid. (16) Using a sterile cotton swab, the ring of spinach debris around the upper inside circumference of the centrifuge tube was wiped off and this residue was discarded.

(17) Cold PBS (Fisher, BP-399-1), diluted to 1× with RO water, pH 7.4, was added to fill each 2.0 ml microcentrifuge tube. (18) Samples were vortexed for 1 min to increase diffusion of any remaining phloxine B or Percoll from particles or cells into the surrounding liquid; they were then centrifuged at 9,400×g for 6 minutes. (19) Supernatant was decanted, leaving behind a phloxine B- and Percoll-free pellet containing mostly non-fluorescent particles (bacterial cells and residual spinach); the volume in each centrifuge tube was brought up to 1.0 ml using ca. 900 µl PBS. (20) The pellet was broken up using a pipette tip that fit all the way to the bottom of the centrifuge tube. (21) 240 µl of RAPID-B Reagent B and 10 µl of Reagent A were added to each sample and the tube was capped.

(22) Samples were incubated for 5 minutes at ambient temperature with gentle vortexing (25% setting on a Vortex Genie 2, Daigger). Control of reagent incubation time is important to maximize target cell tagging while minimizing tagging of cross-reactive non-target bacteria. In normal operation, samples are introduced for analysis immediately after vortexing. If for any reason much time elapsed after vortexing, the sample was shaken again to homogenize the cell suspension.

Improved RAPID-B Method, Follow-Up Validation, Very Low Level Target Cell Numbers The follow-up validation used the same steps as above under Improved RAPID-B procedure—preparation and analysis of samples with some variations as follows. The positives contained only 3-4 target cells. The virulent strain of *E. coli* O157:H7 (ATCC 43895) possessing both ST1 and ST2 shiga-like toxin genes was used as the target organism. *Enterobacter cloacae* (ATCC 35030), rather than a non-O175 *E. coli*, served for the competitor organism. The work included only two inoculation levels: 6 blank samples inoculated with sterile PBS blanks and 12 nominally positive samples. The sample panel (RAPID-B only) comprised (6+12)=18 plus 7 more, a total of 25 samples. The 7 extra samples comprised 6 for addition of the competitor microorganism at a supra-specification goal of ca. 20×(actual 18.75×) the low target level, and 1 competitive assay blank. A vacuum-filter step (Steriflip, sterile 20 µm nylon net, Millipore Corp, Bedford, Mass.) was added between steps 12 and 13 to eliminate clogging of the 5 µm pore size filter.

Example 2

Validation Using the Original Protocol

This example describes the results of the validation study using the original protocol.

As shown in Table 2, using the RAPID-B method for the high level inoculations (approximately 22 cells per 25 grams spinach) obtained the correct answer in all 6 samples for 100% accuracy. In addition, the BAM 4a method resulted in the correct answer in all samples. The low level inoculations, as confirmed by a panel of tryptic soy agar culture plates (Difco), averaged 3.2 viable cells per 25 grams. The LITMUS RAPID-B resulted in 4 out of 6 correct answers (67%), while the BAM 4a method resulted in 3 of 6 correct answers (50%). On the blank samples, Litmus Rapid B gave three false positives (50% accuracy) while the BAM method reported all samples negative (100% accuracy).

Although the RAPID-B false positives were a concern, it was concluded that they could have been avoided had the background events associated with old or damaged spinach been reduced.

TABLE 2

Validation Study Results Using Original RAPID-B and BAM, Protocols

| Sample | *E. coli* O157 Inoculation Level, No. | BAM Final Conclusion | LRB Final Conclusion | LRB Cell Counts |
|---|---|---|---|---|
| 1 | High, 32 | + | + | 120 |
| 2 | High, 32 | + | + | 103 |
| 3 | High, 32 | + | + | 104 |
| 4 | High, 32 | + | + | 99 |
| 5 | High, 32 | + | + | 68 |
| 6 | High, 32 | + | + | 211 |
| 7 | Blank, 0 | - | False + | 87 |
| 8 | Blank, 0 | - | False + | 59 |
| 9 | Blank, 0 | - | False + | 95 |
| 10 | Blank, 0 | - | - | 36 |
| 11 | Blank, 0 | - | - | 19 |
| 12 | Blank, 0 | - | - | 47 |
| 13 | Low, ~3 | False - | False - | 44 |
| 14 | Low, ~3 | False - | + | 63 |
| 15 | Low, ~3 | False - | False - | 49 |
| 16 | Low, ~3 | + | + | 67 |
| 17 | Low, ~3 | + | + | 100 |
| 18 | Low, ~3 | + | + | 89 |

Dot distribution inside the final fluorescence plot suggested that the unexpectedly high counts in RAPID-B fake positive blanks originated from an abundance of fluorescent spinach particles. FIG. 1 indicates the appearance of the light scatter and final screens for a typical spinach blank sample under the original method. The FL1-FL3 screen on the right has 30 counts inside the counting gate, which could be interpreted (incorrectly) as 30 live target cells in the sample. The many dots displayed in a diffuse pattern above and outside of the counting gate, typify fluorescent, non-bacterial particles. The remedies for this situation and their rationales were discussed in above (Example 1: Procedure improvements).

Example 3

Limit of Detection Results for the Improved Method

The detection limit experiments described in Example 1 (Threshold definition, counts-to-threshold ratio, limit of detection and time-to-results) were conducted by the originating laboratory personnel, not by the external laboratory.

The results are shown in Table 3. Average inoculation values reported in the upper row of Table 3 are $\frac{1}{6}^{th}$ of counts determined by plate counts for the inoculation suspension added to the 450 ml of broth: e.g., 140/6=23.3; 80/6=13.3, etc.

TABLE 3

Method Limit Of Detection ($LOD_{RAPID-B}$) results for the improved RAPID-B *E. coli* O157 method.

| | Plate Count Average Inoculation per 25 g spinach | | | | | |
|---|---|---|---|---|---|---|
| | 23.3 (Cells) | 13.3$^a$ (Cells) | 4.4 (Cells) | 0.7$^b$ (Cells) | 0.11$^b$ (Cells) | 0.05 (Cells) |
| Most Probable Fraction Positive | 6/6 | 6/6 | 6/6 | 4-5/12 | 1-2/12 | 0/6 |
| Observed Fraction Positive | 6/6 | 5/6 | 6/6 | 2/12 | 2/12 | 1/6 |
| Observed Fraction True Positive | 6/6 | 5/5 | 6/6 | 2/2 | 2/2 | 1/1 |

$^a$1 of 6 replicates was confirmed as negative, whether by chance or experimental error; hence the bottom row numerator at the 13.3 cell inoculation level is only 5.
$^b$Results from 12, rather than 6, replicates.

In the bottom row of Table 3, the numerator value appears in 4 cases as fewer than 6 or 12 because analysis after overnight culture of the remaining enrichment from nominally positive analytical samples reporting negative results, confirmed them as true negatives. Since they were true negatives, they were not reported as false negatives for LOD determination. The bottom row fractions show that the RAPID-B method consistently detects 1 or more viable and culturable cells of *E. coli* O157 in raw spinach. Further, there were no samples confirmed as true positives but RAPID-B negatives after the 6 hour growth. That is, if executed by experienced personnel, the complete method including enrichment had no fractional recovery level other than absence of any target cells. Thus it was concluded that method $LOD_{RAPID-B}$ in raw spinach is one viable, culturable cell.

Example 4

Validation Using the Improved Method

This example describes the results of the validation study using the improved protocol where food particles were photobleached using phloxine B.

For all target microbial inoculations (14 or 122 cells per sample), both RAPID-B and FDA BAM reference methods reported positive analyses except for a single 14 target cell plus 5× competitor BAM sample. Because there was only one such sample, it was not clear whether the false negative result represented onset of BAM fractional recovery or an anomaly.

As shown in Table 4, the target was *E. coli* O157:H7 (ATCC 43888) and the competitor was non-O157 *E. coli* (ATCC 35421). The symbol "+" indicates a positive result for the sample; "−", a negative result. Samples in which the original results were ambiguous (counts numbering 4-18) were reanalyzed after an additional two hours' incubation. Such counts and re-counts (Heading "C'ts; R-cts") are shown, separated by semicolons, in the right-most column. In the table, the grey background cell highlights a false negative result by BAM.

TABLE 4

Results for the improved RAPID-B *E. coli* O157 method, first validation study.

| Sample Number | Sample Code BAM | Sample Code RAPID-B | *E. coli* O157 Inoculation Level, No. | Correct Sample I.D. | BAM I.D. | RAPID-B I.D. | RAPID-B Cell Counts (C'ts; Re-c'ts) |
|---|---|---|---|---|---|---|---|
| 1 | D1 | B4 | High, 122 | + | + | + | 5634 |
| 2 | D3 | A7 | Low, 14 | + | + | + | 1909 |
| 3 | C1 | A6 | Blank, 0 | − | − | − | 1 |
| 4 | B6 | A5 | High, 122 | + | + | + | 6180 |
| 5 | B7 | C3 | Low, 14 | + | + | + | 1709 |
| 6 | D6 | B8 | Blank, 0 | − | − | − | 2 |
| 7 | C4 | A4 | High, 122 | + | + | + | 3808 |
| 8 | A3 | B1 | Low, 14 | + | + | + | 710 |
| 9 | A2 | D4 | Blank, 0 | − | − | − | 10; 4 |
| 10 | B2 | B3 | High, 122 | + | + | + | 3629 |
| 11 | A9 | B9 | Low, 14 | + | + | + | 3455 |
| 12 | E4 | C5 | Blank (Comp.), 0 (70) | − | − | − | 1 |
| 13 | C6 | C7 | High, 122 | + | + | + | 11756 |
| 14 | C8 | C9 | Low, 14 | + | + | + | 23; 7264 |
| 15 | A8 | D9 | Blank, 0 | − | − | − | 0 |
| 16 | D2 | D8 | High, 122 | + | + | + | 26529 |

TABLE 4-continued

Results for the improved RAPID-B *E. coli* O157 method, first validation study.

| Sample Number | Sample Code BAM | Sample Code RAPID-B | *E. coli* O157 Inoculation Level, No. | Correct Sample I.D. | BAM I.D. | RAPID-B I.D. | RAPID-B Cell Counts (C'ts; Re-c'ts) |
|---|---|---|---|---|---|---|---|
| 17 | B5 | D7 | Low, 14 | + | + | + | 661 |
| 18 | D5 | C2 | Blank, 0 | − | − | − | 10; 7 |
| 19 | A1 | E1 | High, 122 | + | + | + | 20419 |
| 20 | E2 | E3 | Low (Comp), 14 (70) | + |  | + | 16; 2047 |

FIG. 2 indicates qualitatively the contribution to improvements attributable to phloxine B-sensitized photobleaching. The appearance of events in the 2D light scatter gate on the left is essentially unchanged as a result of the treatment (compare to FIG. 1), but on the right, fluorescence has been all but eliminated and the number of events in the counting gate is zero for the blank sample.

FIG. 3 shows the resulting appearance of a blank spinach sample when a gradient centrifugation step alone was used to decrease the number of food particles passing through the instrument.

Figure 4:
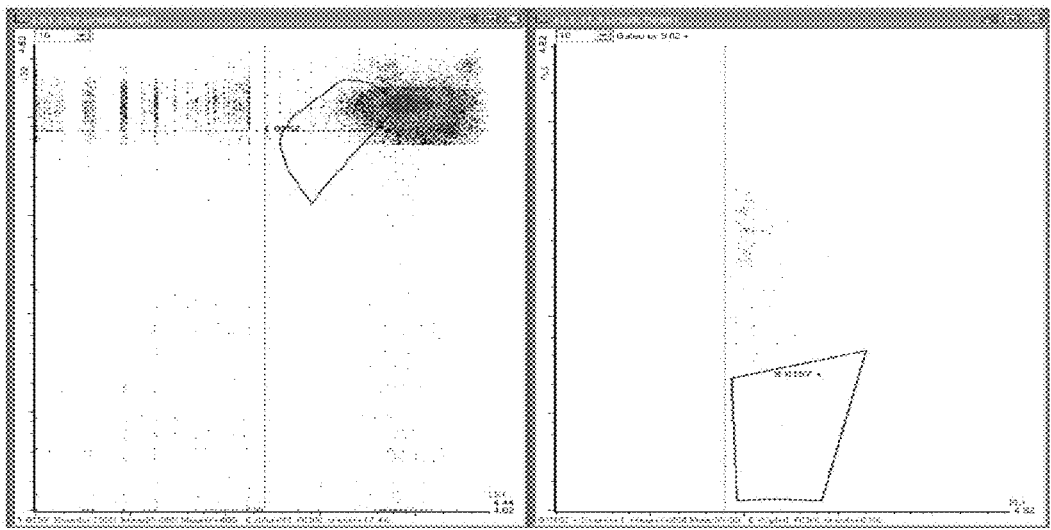
FIG. 4 shows typical analysis of a 5-µm filtered spinach blank treated with phloxine B and light per the improved method followed gradient centrifugation to eliminate approximately 98% of the spinach particles. Even though most particles did not fluoresce after photobleaching, reducing the particle load was desirable because their presence increased instrument flow path contamination.

FIG. 4 shows a blank spinach sample when both photobleaching and gradient centrifugation were combined, the latter to decrease the number of spinach particles passing through the instrument.

Based on N=19, as determined before the validation was initiated, the background for the improved method averaged 2.2 counts, standard deviation was 2.9, and threshold was 11.

Figure 5:
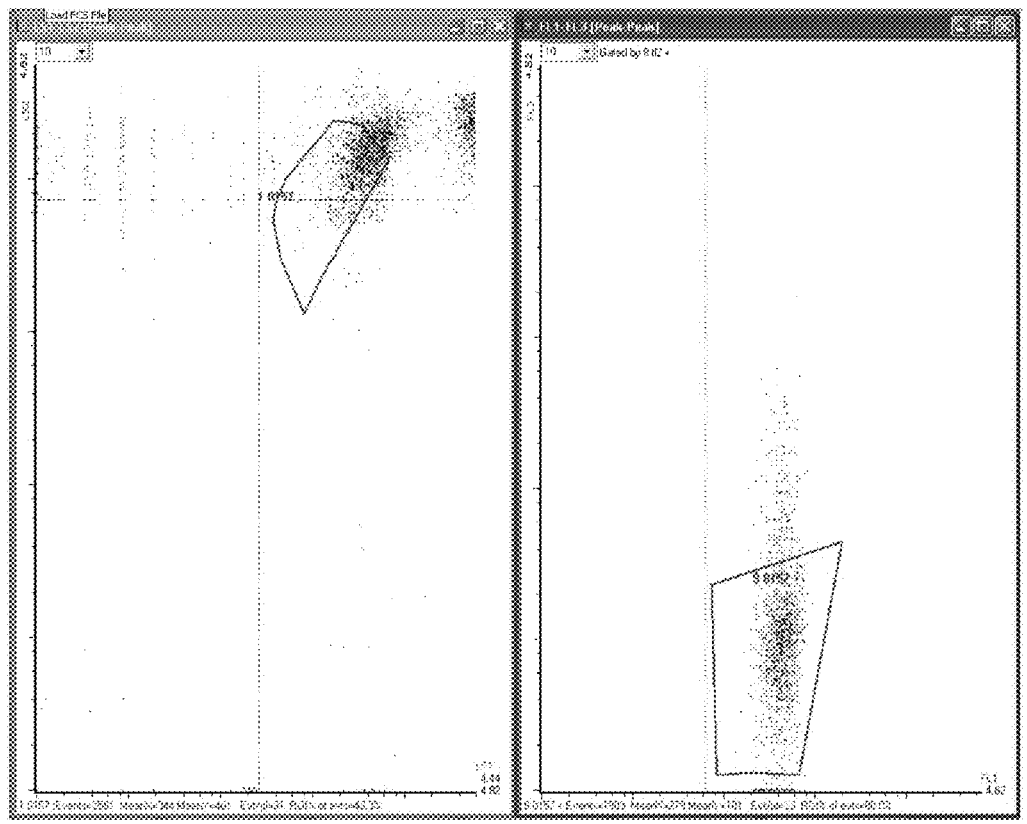
FIG. 5 shows two dot plot screens 2, RAPID-B code A7, a low level (ca. 14 cells positive plus added competitor (non-O157 *E. coli*, ATCC 35421, ca. 70 cells) spike during the validation. 1909 target cells were counted.

FIG. 5 shows results for a low-level spike (ca. 14 cells) with added competitor (ca. 70 cells) after 5 hour enrichment and sample treatment using the validation protocol.

Photobleaching reagent concentration, light source, and exposure duration were optimized for the validation. 94% of the target cells were counted as viable even after the light exposure, sample concentration, gradient centrifugation, and incubation steps. The elapsed time after light exposure for late samples in the queue was as much as 1 hour from light exposure to analysis.

Example 5

Follow-up RAPID-B Method

In the follow-up experiments, triplicate trypticase soy agar media (Difco) confirmed the inoculation levels as 4.0±2.6 culturable cells for the *E. Coli* O157 target and *Enterobacter cloacae* competitor as 73.3±27.3 per 25 g spinach.

The expert threshold was determined as T=6 based on N=17 blank analysis.

Run by expert analysts, the RAPID-B method for single cells had not experienced partial recovery (Example 3). Executed by inexperienced analysts it did not fail for low triple and double digit target cell inoculation levels (Example 4). It did not break down in the follow-up test study (Example 5): with single digit inoculation levels, RAPID-B experienced no false negative results. 16 of 18 nominally positive samples were identified. Two positives reported as negative by RAPID-B were established as true negatives upon confirmatory analysis.

The RAPID-B method reported two false positive samples relative to the sample key. In one case, the competitor blank, the original sample was indeed blank as determined upon reanalysis. Close examination suggested the false positive was possibly the result of cross contamination during sample processing. This positive inference was based on screen shot characteristics. The possibility of cross contamination was based on observation that one of the sterile vacuum filters remained unused at the end of the day, indicating that another filter (numbers counted out before analysis began) was used for two samples. This evidence was combined with the unexpectedly low number of counts on analysis, indicative of real target contamination from a positive sample, cells introduced during preparation steps without time or conditions for them to multiply.

The other false positive was a Blank that was confirmed positive upon reanalysis. Analysis and reanalysis reported the expected number of target cell counts for an initial low level contamination.

Figure 6:
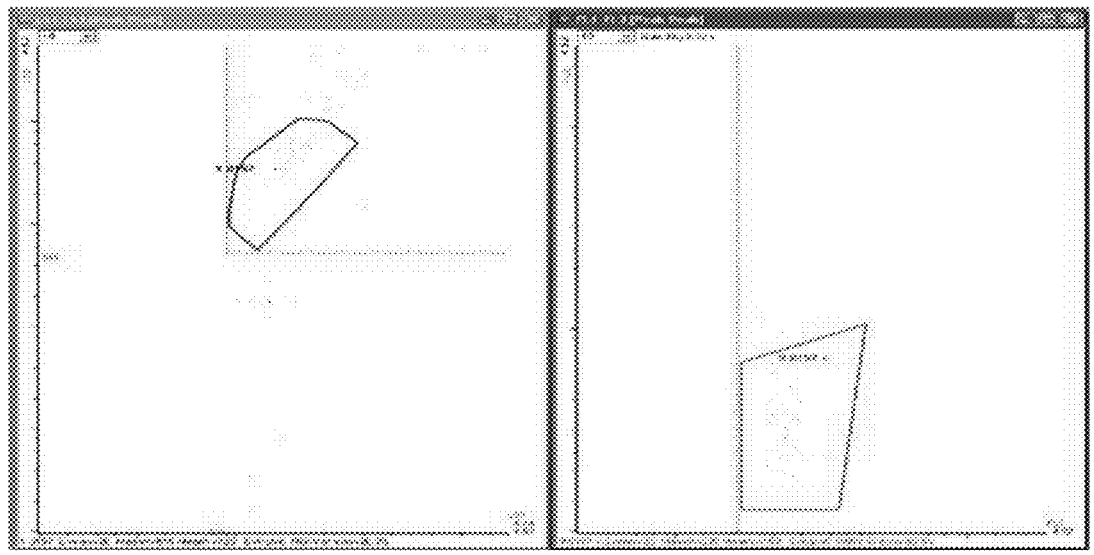
FIG. 6 shows two dot plot screens RAPID-B sample B1, the competitor blank. The screens do not indicate sample matrix overrun and the counted dots, both in their position within the fluorescence counting box, the proportion of dead to live events, and their spatial distribution look like *E. coli* O157 evaluated under the photobleaching method.

Thus, the RAPID-B follow-up test returned two false positive results. RAPID-B sample B1 was a competitor blank: it should have contained no *E. coli* O157 cells but many, ca. 73, of the *Enterobacter cloacae* competitor. The correct answer was negative. Using an expert threshold definition, T=6, the 23 counts observed would have been a false positive. Using the beginner threshold, T=100, the sample would have been declared negative and would have raised the RAPID-B performance statistic after confirmation to 96% correct. However, examination of the F11 vs. F13 dot plot (FIG. 6) did not indicate that the 23 events were intruding background due to beginner sample handling technique. Rather, the dot cluster pattern was one typically associated with a true *E. coli* O157 positive.

Cross-reactivity of the *E. coli* O157 antibodies for *Enterobacter cloaecae* has been ruled out as an explanation for the 23 counts. Intruding spinach background does not explain the 23 counts. Neither are 23 cells what one would expect, even under a scenario of growth depressed by a competitor. Cross-contamination within the instrument from a previous positive sample might explain this result. The sample processed immediately prior to this was a positive showing over 1000 counts. However, the instrumental method uses multiple wash steps between samples and cross-contamination in the instrument is not usually observed unless a previous sample contained ca. 500,000+ target cells. The improved method uses multiple pipette and filter operations on each sample. It is hypothesized that either (1) a pipette tip used on a preceding positive sample was not discarded and was reused along the way for this sample [but such a mistake was not observed by the experts] or (2) the analyst was depressing the pipette sample plunger too far and thus drew a preceding positive sample beyond the disposable tip into the pipette barrel or (3) a filter from a previous positive run was re-used. For any of these actions, the cells, thus introduced, would not have time or conditions for multiplying, so could well be present as carry over into a succeeding sample. They would be seen in relatively small numbers compared to the 500+ expected for a real contamination followed by enrichment. These explanations demonstrate the capacity for troubleshooting and sample verification implicit in the high information content provided by the rapid system. This information resides not only in the quantitative reports from the counting region but also the visual characteristics of the display.

Based on qualitative features in the sample analysis screens, it is likely that both samples were true positives: one due to contamination during RAPID-B sample processing and the other due to contamination during initial preparation by the third lab. If so, the RAPID-B instrument reported 100% correct identification in all 25 samples. A 92% accuracy is reported herein without excusing the two nominally false positives.

Example 6

Methods of Separating Bacteria from Particulate Matter

This example provides methods that can be used to prepare a sample for analysis with the disclosed methods. For example, after incubating the sample with the culture medium to allow the bacteria in the sample to grow and replicate, and adding the photo-sensitizing agent, the samples can be processed as described in this example (e.g., the centrifugation and filtration methods) to remove undesired non-bacterial sample particulate matter and mitigate the effects of interfering food components.
Materials and Methods
Methods of Analysis

*E. coli* serotype O157:H7 isolate, ATCC 43888, which does not produce Shiga-like toxin I or II, was used. The foods tested were raw spinach, horseradish sauce, baby foods (bananas, peas, carrots, and beef/gravy), apple juice, pear juice, peanut butter, half-and-half, 2% homogenized milk, processed cheese sauce, mayonnaise, chocolate ice cream, and tartar sauce.

Two reagents, Reagents A and B (LITMUS RAPID-B, Little Rock, Ark.) were added to the sample. Reagent A contains fluorescein-conjugated, purified polyclonal antibodies that target epitopes uniquely associated with the cells of interest, in this case *E. coli* O157. The antibodies were immuno-purified for use in the RAPID-B *E. coli* O157 assay by standard techniques. The efficacy of the purification was demonstrated by Inclusivity and Exclusivity studies, as reported in the previously cited FERN 2 validation study (Owens, 2009). The antibody reagents are substantially more dilute than for non-cytometric immunity-tagging assays. Reagent B contains detergents and other ingredients that prepare bacterial cell surfaces so that their epitopes are accessible. The same formulation for Reagent-B is used for other RAPID-B pathogen-specific assays.

A RAPID-B model 9013 flow cytometer (LITMUS RAPID-B) was used. Excitation is by a solid state 20 mW 488 nm laser. Emission was detected at the standard FL1 (525 nm), FL2 (600 nm), and FL3>670 nm) frequencies. Photomultiplier tubes were used for all light scatter and emission detection. The electronic gains and voltages are factory calibrated so that, for any specific RAPID-B assay (such as *E. coli* O157), the transmitted and excluded events are the same and the same gate definitions can be shared among model 9013 instruments. Compared to other commercially available instruments, this instrument has superior optical and physical characteristics (130 nm resolution, a very large cross-section flow cell channel, and syringe-controlled sample introduction) for detecting and quantifying bacterial sized particles in complex matrices. Data retrieval requires no post-processing; all signal processing is accomplished and results are displayed immediately for the portion of the sample suspension analyzed.

The final cytometer gate was displayed graphically as a trapezoidal region within a two-dimensional dot plot (FL1 vs. FL3, peak-to-peak), each dot representing an event that had passed through a series of seven prior gates. These gates are two dimensional combinations among the peak area and peak-to-peak outputs of the five photomultiplier tubes (the low angle and high angle scatter as well as the three different fluorescence emission wavelengths). If an event arose from detection of an *E. coli* O157 cell, its dot appeared inside that trapezoid if the cell was alive but above it on the same plot if it was dead. (A dead cell's membrane is compromised so that the propidium iodide counter-dye penetrates and increases the excitation signal in the FL3 wavelength for that cell.) The instrumental protocol was set to count viable target cells (with each cell represented on the display as a dot inside the trapezoid).
Metrics for Evaluating the Significance of Flow Cytometric Analysis False-positive events can be characterized by the probability of their occurrence (Henery et al., 2008) and distinguished by their appearance within the final counting gate of a dot plot display. Using such information, it is possible to define both intrinsic and practical limits of detection (LODs) and estimate the TTR.

The probability of false-positive events was based on reagent method blank replicates. For such analyses, a threshold was calculated from the number and variability of counts for the blanks: average blank counts plus $3\sigma$. An analytical ratio called the counts-to-threshold ratio (C/T) was defined. C/T is analogous to the familiar signal-to-noise (SN) ratio. However, significant results are assigned for S/N>3 to 10. Because threshold incorporates variability and is approximately three times greater than background, C/T is a statistically significant positive result for any number of counts greater than the threshold, i.e., for C/T>1.0.

The flow cytometer counts events. For a particular analysis, false events do not differ greatly from true events in the amplitude of fluorescence emissions. (Events that contribute to the final count will have met all serial gating criteria.) If there are at least 10 counted events, false signals can be distinguished from true signals by one significant difference: the false counts, though lying within the dot plot's counting gate, do not form a cluster within it. Together, C/T and dot plot clustering address the question of confidence that nominally positive results are true.

For a food presenting minimal matrix interference, the LOD is a function of the target cell concentration, sample size collected, efficiency of target cell recovery during preparation, and sample volume analyzed. For short-term enrichment of cells spiked into food, additional factors affecting LOD and/or TTR include the lag phase duration, early log phase cell division rate, food matrix interference, and enrichment time.
Decreasing TTR for Extreme Sensitivity Requirements To reduce lag phase and increase division rate of environmentally stressed *E. coli* O157 cells, the sample was cultured in brain heart infusion (BHI) (FDA, 2009b), from Becton Dickinson and Co (Sparks, Md.) at 42° C. The faster the target bacteria replicate, the less time passes before their number exceeds threshold and C/T>1.0.
Reduction of Physical and Optical Interference in Difficult Food Matrices Interference from food matrix components affects the threshold factor (denominator) of the C/T ratio. Reduction or elimination of background counts increases the C/T and facilitates methods with shorter TTR. Methods tested included filtration, background signal bleaching (using 5% sodium carbonate), centrifugation with decanting to rinse out soluble food components, and density gradient centrifugation (Lindqvist, 1997; Uyttendaele et al., 1999). For milk-based and other fat products curdling by addition of 0.1% HCl to the sample was used to produce two separate layers: a bacteria-containing aqueous lower layer and a fatty upper layer. Syringe filters were tested for transmitting *E. coli* while excluding food particles; membranes of 1.0-µm pore size polyether sulfone, 2.7-µm glass fiber, and 5.0 µm polyvinylidene fluoride (PVDF, for low protein binding) were tested.

Sample handling processes suitable for analyzing 14 of the 15 food types were surveyed. Many are well known in food analysis and do not require detailed explanations. Some procedures less commonly used for food analysis are detailed in the raw spinach analysis protocol, which substitutes a four-hour enrichment for the overnight growth previously used (Owens et al., 2009). The 15$^{th}$ food type was raw spinach and an experimental design and an SOP for its analysis are described below.

Background reduction techniques included physical processes commonly used in food sample preparation such as filtration and centrifugation with decanting. Other less common sample treatment processes included suspension of cells and food particles by agitation in a mutually immiscible vegetable oil/aqueous liquid mixture for hydrophobicity-based separation (conceptually similar to liquid/liquid extraction), buoyancy gradient centrifugation, addition of dilute hydrochloric or phosphoric acid to "curdle" milk proteins and fats, and oxygen bleaching (using 5% sodium carbonate). Finally, signal filtering techniques (extending beyond the scale of software functions commonly used for analysis of flow cytometric data) were optimized for the challenges presented by some of the food matrices.

Solid and semi-solid foods were subjected to pre-filtration treatments, including:
  Dilution 10× or 100× with PBS, blending or vortexing to homogeneity, settling for 5 min with aspiration and retention of the supernatant,
  Two minute pulsification using a model PUL 100 pulsifier (Microbiology International, Frederick, Md.), and/or
  Coarse filtration (330 µm pore size) using Whirl-Pak filter bags (Nasco, Fort Atkinson, Wis.).

The experiments used the RAPID-B *E. coli* O157 data acquisition protocol and evaluated 100 µL suspensions prepared from unspiked food. *E. coli* O157 detection reagents were not added to these blanks, so that measured counts would represent events arising from the food matrix itself, not any incurred bacterial residues.

Experiments with *E. coli* O157 and the reagents showed no binding to non-target cells or food particles. There was no difference in the number of counts for negative controls, whether or not the reagents were included in the assay, so the solid and semi-solid food background results were not compromised by the decision to run them without including the *E. coli* O157 targeting reagents. However, for the raw spinach protocol, experiments designed to the architecture of a FERN 2 validation protocol, the specified reagents were used in all experiments, including the background and threshold determinations as well as for each sample, even blanks since identity was unknown.

Multi-dimensional Data Analysis Techniques for Reducing Matrix Background

Food matrices that are difficult for flow cytometry are so classified because they produce large numbers of particles in the size range of bacteria and these particles also autofluoresce to give signals that can mimic the target bacteria. Typically such particles occur in a wide range of sizes. The challenge of excluding such false signals while accepting signals from the target can be addressed by electronic filtering of the available signals. No matter how efficient the filtering, some false signals will closely emulate those from the target, and the analytical challenge devolves to battling statistics. 99.99% filtering efficiency will still probably accept 100 out of 1 million false signals.

The RAPID-B system has five independent detectors. Two sense, respectively, the low and high angle scatter of the incident light from small particles passing through the flow cell; the other three are arranged as is common for flow cytometers to detect fluorescent light emitted by the particles at shorter wavelengths. These five detectors each have two ways of reporting signal. One is peak-to-peak and the other is based on peak area. The two signals are somewhat but not completely correlated. The former represents the highest intensity of light signal for one event and the latter, a combination of light intensity and duration. These values respectively correspond to: (a) the gross size of particles or their number of fluorescent tags (or their natural fluorescence for matrix), and (b) the particle proportions (a significant and reproducibly distinctive feature for bacterial cells). That is, there are 5×2=10 dimensions of scattered or emitted light associated with each discrete event. Most RAPID-B data acquisition protocols, including that for *E. coli* O157, have been designed as a series of eight to eleven gates, each a two dimensional polygonal region drawn in the plane of two of the ten dimensions. A non-expert user would observe only the first and final gates in the series. For each of the RAPID-B assays, these multiple serial gates have been factory defined to include detection of the designated target cell type and to exclude all other signals. The shapes and sizes of regions are determined empirically. Data acquisition methods can be transferred between RAPID-B cytometers because the instrumental design allows for matching performance between instruments and because, once calibrated, the instrument does not require field adjustments. The gating architecture can also be used to exclude events from confounding matrix particles. The *E. coli* O157 assay used eight serial gates.

Analysis after Recovery from Raw Spinach and Short Period Enrichment

To simulate conditions at a packaging plant, methods were investigated to determine how quickly a definitive screening analysis for *E. coli* O157 on raw spinach can be completed. Since use of the method for incurred contaminants would necessarily involve cells adjusting to a changed nutrient source, the cells used for inoculation were grown in TSB, not BHI, and were refrigerator-stressed for 4 days before use. Because maximum sensitivity was needed for detecting low level contamination, the cytometer was rigorously cleaned using standard protocols to lower background before the tests were started.

18 samples of fresh spinach (25 g each) were spiked, using six replicates at three levels (blank, low=~5 stressed *E. coli* O157 cells, and high=~50 of the cells). These levels were chosen based on FERN validation specifications that accuracy for a rapid method be tested at two levels an order of magnitude different, in which the lower level is that at which the tested method (or reference method) begins to give fractional recovery (sporadic false negatives). The RAPID-B instrument was used to estimate the *E. coli* O157 concentration in the inoculating broth so that 100 µL of PBS would contain approximately 50 cells. A 10× dilution of this suspension was then made. High level spiked spinach samples had 100 µL of the concentrated suspension (~50 cells) deposited on the leaves. Low level samples had 100 µL of the dilute suspension (~5 cells) added. Sterile PBS (100 µL) was added to each of the blanks (non-inoculated controls). After deposition, the leaves were gently massaged in the sealed plastic bag to spread and rub in the solution. The spiking level was quantitatively determined by plating the high level spiking solution on tryptic soy agar plates (Difco) at the time it was used.

Experimental (SOP) for the Raw Spinach Method

The amount of time to complete each step is shown in parenthesis after the step. Spinach leaves were aseptically divided into 25 g aliquots, placed into Whirl-Pak filter bags, spiked with bacteria using 100-4 volumes, and the deposited suspension lightly rubbed into the leaves (2 minutes each). 75 ml of sterile, preheated 42° C. BHI broth was added to each sample, and the sample incubated at 42° C. (1 minute each). After a 4-hour incubation, 37.5 ml broth from each bag was transferred into a 50-ml polycarbonate centrifuge tube and centrifuged at 16,200×g for 20 minutes (for batches of eight, 2.5 minutes per sample). The supernatant was decanted, leaving 900 µL of BHI and pellet (30 seconds each). The pellet was suspended in the 900-µL volume by vigorous vortexing (30 seconds each). 600 µl buoyancy gradient solution (Lindqvist, 1997) was added to a clean 1.5-ml centrifuge tube (30 seconds). The 900-µl suspended pellet is layered onto the buoyancy gradient solution without mixing the two layers (1 minute). This was centrifuged at 15,100×g for 1 minute (batches of up to 24 samples, but assuming only 4 samples, average 15 seconds each). From the top, all but 100 µl was removed, 800 µl sterile PBS added, and cells suspended by vortexing (1 minute). This was centrifuged at 15,100×g for 2 min; (batches of up to 24 samples, but assuming only 4, average 15 seconds each). The supernatant was decanted leaving 10 µL, 740 µl of sterile PBS added, then vortexed (2.5 minutes each). This was filtered using a syringe (5-µM pore size, 30 seconds each).

Reagents A and B were added, followed by ambient incubation (~25° C.) with tagging reagents under gentle vortexing (5 min).

Results

Decreasing TTR for Extreme Sensitivity Requirements

*E. coli* O157 cells cultured in BHI at 42° C. multiplied more quickly than cells at other temperatures or in other media. Upon incubation under these conditions, the lag phase for cells that had been refrigerated in TSB overnight was 2 h 10 min and the replication period in early log phase was about 40 min. After a total of 4 h each *E. coli* cell would be expected to divide almost three times, producing eight cells. Eight cells could be distinguished from a blank sample only if they were collected efficiently, perhaps concentrated into a small volume, and if the background and threshold counts from the food were almost zero. This situation was used to evaluate background reduction in various foods.

Reduction of Physical and Optical Interference in Difficult Food Matrices

Several effective techniques reduced interference from food particles. Background reduction used combinations of techniques that varied depending on the food. Each post-filtration technique was independently tested to assure good recovery. Bleaching with sodium carbonate did not adversely affect the RAPID-B fluorescence probes. However, it rendered bacterial cell membranes porous so that the impermeable DNA-intercalating dye, propidium iodide, in the Reagent B could penetrate, thus registering all cells as non-viable.

Filtration

All foods required fine membrane filtration, for example to prevent clogging of the cytometer flow cell. Of the membranes tested, the best combination for efficient target cell transmission and maximum food particle exclusion was obtained using 5-µm pore size PVDF (Millex-SV, 25 mm diameter, non-sterile, PVDF "Durapore", Millipore Corporation, Bedford, Mass.).

None of the foods tested inhibited the RAPID-B fluorescence tagging chemistry.

Apple Juice

Clear apple juice presented little challenge for flow cytometric analysis. A 1 ml sample was passed through the 5-µM pore size, 25 mm PVDF syringe filter into a 2 ml microcentrifuge tube, loaded directly into the flow cytometer and 100 µL were analyzed. The background events numbered zero and the standard deviation was zero. (Therefore, the threshold would be, by convention, 1. In analysis of apple juice, any number of counts in excess of 1 would be regarded as potentially positive for the target analyte.)

Ground Beef

Preparation for analysis of ground beef was as follows. 25 g samples were added to 75 mL of sterile PBS in a Whirl-Pak filter bag, and pulsified for 1 minute. Sampling beyond the filter gave a suspension which could be passed through a 5-µM pore size syringe filter and, after a five minute incubation, analyzed by the flow cytometer. However, a blank sample of this suspension produced 556,000 false positive counts, without immuno-labeling reagents. Two cycles of high speed centrifugation with decanting of the supernatant were followed each time by addition of PBS to the recovered pellet. The resulting matrix effects were diluted so that only one count was observed. This not only diluted matrix contributions but, if larger starting volumes were selected, would concentrate target bacteria and increase analytical sensitivity for detecting targets. Buoyancy gradient centrifugation used with ground beef yielded RAPID-B blanks averaging only 0.8±0.8 counts, not substantially better than the simpler high speed centrifugation method.

Baby Food Purees (Bananas; Beef+Gravy; Carrots; Peas)

The four baby foods, viscous semi-liquids, required pre-filtration treatments (1:10 dilution in PBS, 1 minute pulsification, and coarse 330-µM pore size filtration). Bananas and carrots were then 5 µM syringe filtered as before; the analyses counted, respectively, 6 and 6,804 false positive events, without immuno-labeling reagents. When the same two diluted sample suspension were subject to gradient centrifugation between filtration and analysis, the false positive events were reduced to 0 and 3, respectively. Dilution would reduce analysis sensitivity by an order of magnitude, so an LOD in the low double digits for analysis by this method is expected, if no high speed centrifugation step were included.

FIGS. 7A and 7B show two screen shots, a blank run for uncontaminated baby food (carrots) showing (FIG. 7A) 6804 counts with 5-µm filtering alone and (FIG. 7B) only 3 counts when buoyancy gradient centrifugation was added.

Analyses of beef+gravy and peas both used a gradient centrifugation step, followed by 5 µm fine filtration. In each case the number of false positive event counts was zero.

Chocolate Ice Cream; Half and Half; 2% Milk; Peanut Butter

Each of these products used the three pre-filtration treatments described above. In addition, curdling and centrifugation was used to concentrate target cells and separate them from matrix components. The curdling step involved adding 25 ml of 0.1% HCl to 25 ml of sample followed by low speed centrifugation. The lower (aqueous) layer was sampled for the target cells.

In the case of chocolate ice cream, the curdling procedure used addition of a corn oil/0.1% HCl mixture (25 ml of each liquid added to the 25 grams of product). After ~30 sec centrifugation at 3000×g, the aqueous fraction, lower layer, was taken up for analysis. Without enrichment, method blanks averaged 27.5 counts, an undesirably high background.

For the two other milk products and peanut butter, the centrifugation step was performed twice. Curdling and low speed centrifugation with sampling of the aqueous layer, were followed by high speed centrifugation and sampling of the pellet that contained the target cells. The average false positive counts for half-and-half, 2% milk, and peanut butter were respectively 0.5, 0, and 0. Use of bleach the color out of the half-and-half and skipping the curdling step was not successful, yielding 786 false positive counts. Use of gradient centrifugation without curdling for the 2% milk and peanut butter samples yielded 7 and 26 false positive events, respectively.

Horseradish Sauce; Mayonnaise; Processed Cheese Sauce; Tartar Sauce

Each of these four viscous liquids was prepared using the pre-filtration techniques described above, but each was impossible to filter at that point. In all four cases, the use of buoyancy gradient centrifugation at 16,100×g for 1 min produced a clear lower layer after which 5 µm filtration was facile and from which efficient sampling of the target bacteria was possible. The false positive blank counts in these four foods numbered 19, 1, 2, and 0, respectively.

Multi-dimensional Gating Architecture for Electronic Background Reduction

The gating architecture was used to exclude irrelevant signals in all the results described herein. An example illustrates the significance of this approach for food and other high background applications.

Two chocolate ice cream blank samples, after treatment by corn oil/aqueous (PBS) extraction yielded (25+30)/2=27.5±3.5 counts. The RAPID-B system allows for post-acquisition re-analysis of an already acquired sample using a modified protocol. The intervening serial gates were removed and the already acquired data were analyzed under the modified protocol. The 25 and 30 counts had originally come from over 90,000 events that met the first gate criterion and would have appeared inside the final counting gate if the series of other gates had not intervened. These 90,000 events, were a subset of almost 370,000 events from particles in the bacterial size range and this from a sample already processed to minimize background.

Figures 8A, 8B:
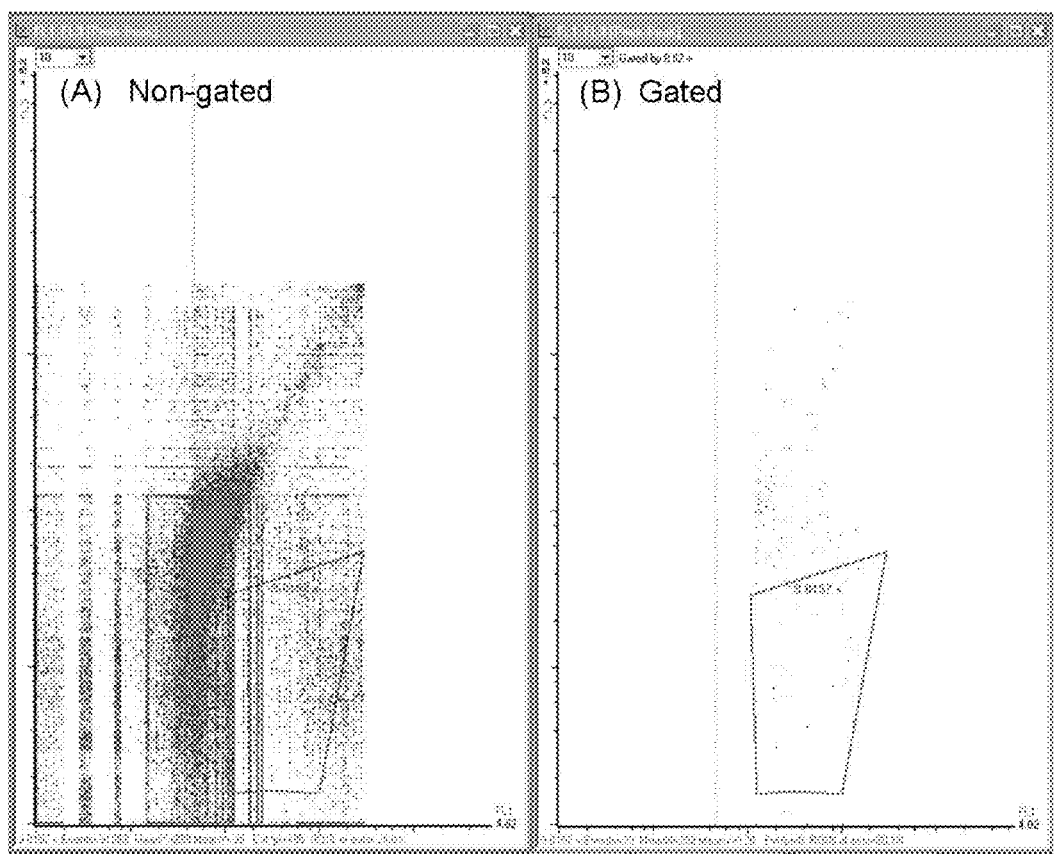
FIGS. 8A and 8B show FL1 vs. FL3 fluorescence plot for a method blank of chocolate ice cream. For the same analytical run, if (A) the serial gates were bypassed, there were 91,063 events in the counting region, and if (B) the gates were not bypassed, there were only 30 events. This represented a >3000:1 ratio of irrelevant/relevant signal exclusion using serial gate signal processing. The lack of a well-defined population in the counting region of FIG. 8B is characteristic of background-associated events, not target cells.

The amount of background reduction possible by electronic gating architecture is illustrated in FIGS. 8A and 8B. This shows the effect of serial gating on background exclusion for a chocolate ice cream blank.

Analysis of E. Coli O157 after Recovery from Raw Spinach and Short Time Enrichment The TTR for analysis of raw spinach was <4.5 h. Based on the average number of colonies from a panel of 4 plates, the inoculation at the high level was confirmed as 76±5 culturable cells. Calculating from the higher level inoculation, the low level was 8 culturable cells. Inferring from the average counts measured by RAPID-B for the low level inoculation compared to that of the blanks, the projected average RAPID-B count for a single viable cell in the initial inoculum after growth was 28, with an estimated C/T of 1.3. This estimate was obtained by averaging the number of counts in the low level inoculations observed after 4 h growth (230), subtracting average background counts (6) and dividing that (224) by the average low level inoculation (8) to give the number of counts (28) expected if only one viable target cell had been in the sample at the beginning. The estimated C/T (1.3) was then calculated by dividing the 28 counts by the Threshold (22).

Figures 9A, 9B:
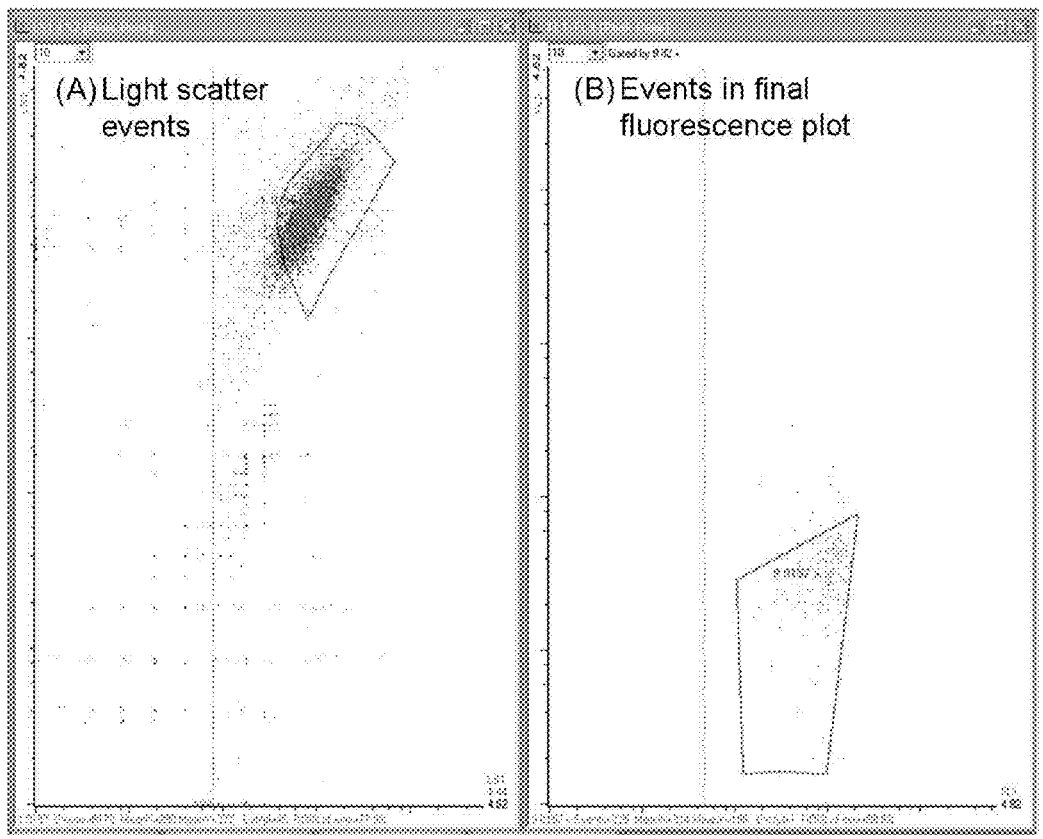
FIGS. 9A and 9B show screen capture images, for a low level inoculated spinach sample after four hours of growth.

FIGS. 9A and 9B display typical results from the raw spinach protocol for a low level inoculation. As shown in FIG. 9B, the final count was obtained after 4 hours of growth in BHI at 42° C. After the average background of 6 was subtracted, this represented 219 cells after growth. The well-defined fluorescent population cluster inside the final counting gate, characteristic of true signal from $E.\ coli$ O157 cells, should be contrasted with the typical diffuse scatter within the counting gate associated with background false positive events (FIG. 8B).

The RAPID-B assay gave a single false negative result for one of the low level inoculations of spinach, thus achieving an overall accuracy of 94%. The missed sample after 4 hours of enrichment had only 13 counts, equal to the highest number observed in any of the six blanks, for which the average count was 6.

Clustering, LOD, and Certainty for Marginal Results

The expected clustering for real events (FIGS. 9A and 9B) could be applied, as a final criterion, to the 4 hour results for the missed spinach sample. Comparison of the final screens reflected the difference between the two samples. For the blank sample, 13 events were spread across the counting gate, whereas 13 tightly clustered events appeared in the upper right corner of the counting gate for the missed sample. (They looked like the cluster shown in FIG. 8B, except that they numbered 13 rather than 225.) Expert interpretation of the final screen would have led to a correct identification for the missed sample.

This discussion of clustering information addresses the question of how few counts can confidently be deemed positive. In these results, clustering of only 13 events was sufficient to differentiate a positive from a blank, even though the C/T definition provided a statistically based measure of certainty, threshold, of 22 for the spinach experiments. However, there is some number of counts, perhaps three to five, where the significance would still be uncertain regardless of clustering, average blank background, or threshold. In a regulatory environment, a preliminary result that a sample is presumed positive requires further analysis for definitive disposition (FDA, 2009b).

Reanalysis of Samples Giving Ambiguous Results

The false negative spinach sample might have been inoculated with fewer than eight $E.\ coli$ O157 cells, maybe even zero. After a lengthened enrichment period for the unused portion, reanalysis confirmed contamination: that RAPID-B sample result for a nominal low level contamination was indeed a false negative. A safeguard was built into the 4-hour enrichment protocol so that the remaining portion of any sample showing from 12 to 48 counts would be automatically returned for 2 hours of additional incubation and then reanalyzed. In this way, false negatives would be eliminated. If spinach or other foods gave an average blank of 6 counts, then the range of ambiguous results requiring reanalysis would be defined as from 12 to 48 counts, that is, two to eight times the average blank. Three of the 18 fresh spinach samples (one the false negative sample; another, a low level inoculation showing slightly fewer than 48 counts; and the third, the 13-event blank) met this reanalysis criterion. Even with 2 extra hours' growth and reanalysis of ambiguous samples, the TTR would be 6.5 hours, less than the eight hour goal.

Assay Selectivity

When the SOP was used for detection of *E. coli* O157 in 25 g of raw spinach after a 4-hour growth period, the results showed a TTR of <4.5 h and a projected LOD of 1 viable cell in 25 g with an estimated C/T of 1.3. Seventeen of 18 samples were correctly identified, based on the number of qualifying counts. The single false negative would have been correctly identified by expert interpretation of clustering within the final counting gate.

Besides physical and chemical sample manipulations, there were other ways in which irrelevant signals were excluded. The use of a series of small gates excluded inappropriate events with high efficiency. Exclusion of non-target background events was efficient and effective, even though the gates transmitted an average of 27.5 qualified but non-target events. Extensive signal processing, independent of the sample preparation techniques and the selectivity of targeting reagents, worked to exclude confounding signals. Use of multi-parametric event exclusion/qualification factors produced a robust analytical system with the accuracy, inclusivity, and exclusivity needed for rapid, sensitive detection of *E. coli* O157 in foods. Many diagnostic technologies used for rapid bacterial detection fail, are compromised, or are slowed when used for food analysis because they do not have a way to exclude false signals or they are vulnerable to interfering matrix constituents (Stevens and Jaykus, 2004; Taylor et al., 2005).

In summary, these results show that for raw spinach analysis, using 4 h culture incubation, the method was 94% correct with one false negative for a low-level inoculation. Its projected limit-of-detection (LOD) was 1 viable cell per 25 g of spinach, based on an average of 28 counts detected after growth and an estimated counts-to-threshold (C/T) ratio of 1.3. These results are generally applicable to any RAPID-B pathogen-specific flow cytometry assay, not just for *E. coli* O157, and not just for food samples.

Example 7

Additional Sample Treatment Methods

This example provides additional methods that can be used to prepare a sample for analysis with the disclosed methods. For example, before or after incubating the sample with the culture medium to allow the bacteria in the sample to grow and replicate, and adding the photo-sensitizing agent, the samples can be processed as described in this example (e.g., the centrifugation and filtration methods) to remove undesired non-bacterial sample particulate matter and mitigate the effects of interfering food components.

It is shown herein that the methods had a linear dynamic range of four orders of magnitude. The RAPID-B method was 100% correct for all samples, whereas the Bacteriological Analytical Manual (BAM) validation method, performed on parallel samples grown overnight, had a 6% failure rate. The limit of detection for the RAPID-B protocol was estimated as a single viable cell in 25 g of ground beef, with counts exceeding the assay threshold by a factor of 16.

Materials and Methods
Basic Sample Handling Procedure

In some experiments, cell suspensions were physically or chemically manipulated to reduce interference. All samples were filtered (5 µM pore size) to prevent clogging the microfluidics and flow cell in the cytometer. Since the fluidic and cell dimensions are relatively large in comparison to bacteria and particles, relatively coarse filtration was sufficient. Typically, 1 ml of filtered sample was added to a 1.5 ml sterile, rinsed microcentrifuge tube with 240 µl of "Reagent B" and 10 µl of "Reagent A." This sample/reagent mixture was lightly vortexed for 5 min.

Instrumental Performance

Experiments used LITMUS RAPID-B Model 9013 flow cytometers (North Little Rock, Ark.), engineered to distinguish bacterial cells and similar sized particles using optimized light scatter architecture, corresponding to forward scatter and side scatter in other flow cytometers. A 488 nm solid state laser individually excited each particle. Light scatter characteristics at 488 nm reflected particle size, shape, and granularity. The sheath liquid was either distilled or reverse osmosis filtered (deionized) sterile water. The reagent-incubated sample was taken up by the flow cytometer (45 sec) and introduced for analysis at 100 µL/min, for either 1 or 2 minutes, depending on the volume analyzed. After analysis, the system initiated two or three flush cycles taking another 60-90 sec. File naming and saving added another 15 sec. Total data acquisition involved <5 min per sample.

Data Acquisition Process

Data acquisition used an instrument control and data acquisition protocol that was particular for *E. coli* O157 target analysis. The protocol specified a number of narrow "gates" (light color and intensity intervals, each of which conformed to the signature of the target bacteria). Based on flow cytometry principles, all light scatter and fluorescence emission responses of each individual particle were compared to serial gate specifications within the range for *E. coli* O157 cells tagged with the specified fluorophore-conjugated antibodies. The number of responses that met all gate qualifications, that passed through all electronic "filters," after subtraction of a threshold value, constituted a count of target cells. Whenever that count was positive, a presumed positive result was reported for the assay. This approach enabled an assay to produce either a qualitative result or, if pre-analysis did not involve a cell culture step, a quantitative result consistent with the 'live' bacterial counts identified within the sample by dilution plating.

Reagent Function

Reagent B contained bacterial cell surface conditioners as well as an FL3 (670 nm) fluorescing DNA dye, to which intact bacterial cells are impermeable (propidium iodide). Reagent A contained FL1 (525 nm) fluorescing molecules conjugated to *E. coli* O157 targeting immunoprobes that attach directly to the surface of target bacteria. The FL3 dye penetrated damaged and dead cells, lighting them with excess FL3 signal. This located their signals outside of the FL1 versus FL3 plot's final gate, so that only live target cells would be counted.

Performance Characterization to FERN 2 Specifications of the RAPID-B *E. coli* O157 Assay Inclusivity for targets was tested with 97 isolates of *E. coli* O157. Exclusivity of non-targets was assessed by 68 bacterial isolates comprising common foodborne pathogens and non-pathogens. The identities of inclusivity and exclusivity isolates are reported in Tables 4 and 5, respectively. Analytical sensitivity in several experiments was reported as counts-to-threshold (C/T), the context for, and definition of which, follow.

Signal was typically 1 count for every "event," a target cell passing through the cytometer flow cell during the analytical run. Analytical noise usually combines anomalies from amplifier electronics with false events arising from non-target signals and, for flow cytometry, carryover of true target cells from earlier analyses. For technical reasons, electronic noise was not an issue in these methods and the only contributions to false positive signal arose from the other two sources: non-target particles for which the light scatter and emission characteristics coincided with those expected for tagged target pathogen cells, and actual target cells left over from an earlier analysis. The term "particle noise" is used to mean either phenomenon.

"Particle noise" counts varied depending on the food being analyzed, how the sample was prepared, and the cleanliness of the instrument. To account for such variables, a threshold was used for the *E. coli* O157 analysis in a particular food matrix for which sample preparation was conducted according to a standard protocol. For simple yes/no results, the threshold would be subtracted from each analysis and only if results were greater than zero would the assay be presumed positive (yes). Threshold was defined as the average background (false signal from blanks) for that food plus three standard deviations of the background. This yielded a threshold for which any number of counts even slightly greater would represent a true positive result in 99% of the cases. This was the lowest possible number of counts for a positive result. Average positives for the experiments below typically had at least 10× higher counts than the lowest possible positive.

This threshold definition allowed further definition of a metric useful for characterizing quantitative analyses. The signal-to-noise ratio (S/N) is the familiar analytical figure of merit in quantitative analysis. A similar metric, counts-to-threshold ratio (C/T), was defined for specific for a particular food type, sample preparation protocol, and set of instrumental acquisition parameters. For a particular combination of factors, multiple method blank analyses gave an average number of false counts and a standard deviation about the average. The C/T for a sample was defined as the number of cell counts less the average of blank run counts divided by the magnitude of the threshold.

Other aspects of RAPID-B system performance were measured: assay repeatability, inter-instrument equivalency, performance stability, linearity of results, and LOD. Nearly 650 RAPID-B assays and 250 dilution plates comprised the overall data set for the FERN 2 validation study. More RAPID-B and dilution plate assays were performed for other experiments reported, such as the ground beef 5 hour short enrichment experiment.

Linearity was assessed without complications from food matrices by comparing reported cell counts to serial dilutions of concentrated target cell suspensions into sterile, filtered 1× phosphate-buffered saline (PBS). In cases where there was minimal food matrix interference, the intrinsic method LOD was a function of the target cell concentration, sample size collected, and sample volume analyzed. For short-term enrichment of cells spiked into food, additional factors affecting LOD and/or TTR included the length of lag phase, cell division rate, extent of food matrix interference, and growth period duration. As mentioned above, the FL3 DNA dye permitted differentiation of viable from non-viable *E. coli* O157 cells.

Absolute sensitivity for the RAPID-B assay was assessed by cell counts per mL analyzed in comparison to colony counts of the same suspensions on agar plates. Because of the inherent quantification variability for plates and to establish a "truth set," individual RAPID-B experiments (cells counted in 100 µL) were plotted against the average of ten replicate plate analyses.

Using the same 10-plate panel experimental design, sensitivity to the presence of non-target microflora was determined by comparing RAPID-B target-cell-counts and plate count results after overnight growth in 25 g of ground beef and 225 mL of growth media. In this experiment, a low level of *E. coli* O157 cells (6-7 CFU/25-g sample) was co-inoculated with *Salmonella typhimurium* cells (65 CFU/25 g sample) as the competitive non-target organism into the growth media specified for the RAPID-B and BAM methods: BHI and tryptic soy broth modified with novobiocin (mTSB-n), respectively.

Validation to FERN 2 Specifications of RAPID-B *E. coli* O157 Assay in Nine Foods Validation of the RAPID-B *E. coli* O157 Assay to FERN 2 specifications, found in "FERN Microbiology Method Validation Guidelines" SOP No. FERN-ADM.0004.00 Dated 10-04-06, was conducted by an independent laboratory. (FERN method procedures are consistent with FDA BAM, AOAC Official Methods Guidelines, and USDA Food Safety and Inspection Service guidebooks and methods. These guidelines are for qualitative analysis by rapid methods.) Parallel samples were analyzed by the rapid method and by reference method FDA BAM 4a, which details regulatory procedures for identification of *E. coli* O157:H7. The reference method in this case used a sequence of culture steps, each taking one day: selective growth on mTSB-n, TC-SMAC Mono Plates, TSAYE Mono Plates, Kovacs Reagent, and EMB Mono Plates.

In all cases, 25 g samples of the food were inoculated with 100 µL of either a 1×PBS solution blank or 1×PBS spiked with a designated *E. coli* O157:H7 test isolate, ATCC 43888, a strain lacking the Stx-1 and Stx-2 Shiga toxin-producing genes. In some cases, the inoculated food was immediately sampled and analyzed. In others, overnight refrigerated storage at 5° C. preceded food sample spiking. Analysis after refrigerated storage emulated environmental stress normally experienced by incurred bacteria in perishable food samples sent to a laboratory for analysis.

The method was validated in nine product matrices: spinach, jalapeño peppers, ground beef, bagged salad, salami, cookie dough, hot dogs, nut meat and beef muscle. Per FERN Level 2 standards, positive inoculations onto the 25 g weighed spinach substrate were executed at two levels: Low, approximately 5 cells; and High, approximately 50 cells.

Analysis after Recovery from Ground Beef and Short-Term Growth

Short-term growth from ground beef contaminated with *E. coli* O157 was evaluated using 25 g samples with three different fat content levels. The 18 samples were spiked at three levels (Blank, Low=5 cells, and High=50 cells) using *E. coli* O157 isolate ATCC 43888 that had been refrigerator-stressed in PBS overnight before inoculation, thus potentially affecting culturability due to low inoculum in combination with cold temperatures (Johnson et al., (1998) *Applied and Environmental Microbiology* 64:4390-4395). The initial inoculation levels were confirmed by the 'average value' of a multi-plate assay, a method shown to yield the best representation of the true inoculation levels. Inoculation levels lower than 5 CFU/mL produced spurious results due either to losses in the sample 'aging' process or to matrix inhibition of bacterial growth.

Each of the samples was placed into a Whirl-pak filter bag and 75 mL BHI broth at 42° C. was added. This was enough broth to immerse the food product but much less volume than the 9:1 broth:food ratio specified in BAM methods. Samples were incubated at 42° C. for 5 hours. Pre-analysis steps used are listed below. After preparation, each sample was analyzed. The unused portion was moved to a second RAPID-B flow cytometer and reanalyzed to assess quantitative consistency between instruments.

For ground beef analysis, preparation steps and their times were as follows. 5 µM pore size filtration of a 15 ml BHI broth aliquot, using a 25 mm syringe filter with PVDF membrane (30 seconds). The resulting sample was centrifuged at high speed (11,500×g) to concentrate cells (10 minutes for batches of 8, or just over 1 minute each). To remove, background interference the supernatant was decanted, leaving 0.1 ml that contained the concentrated cells (1 minute each). The cells were resuspended by vigorous vortexing (30 seconds each). 10 µL of this concentrate was added to 740 µL of 1×PBS, 240 µL of Reagent B, and 10 µL of Reagent A, followed by gentle vortexing and ambient temperature incubation (5 minutes).

Results

Performance Characterization to FERN 2 Specifications of the RAPID-B *E. coli* O157 Assay Tables 5 and 6 contain inclusivity and exclusivity results, respectively, for isolates from the collection of the Arkansas Department of Health.

TABLE 5

Inclusivity for RAPID-B *E. coli* O157 assay

| Stock number | Bacteria | ATCC or ADH ID | Dilution used | Run 1 (# of cells) | Run 2 (# of cells) |
|---|---|---|---|---|---|
| E3 | EHEC O157:H7 | 43888 | $10^{-5}$ | 1099 | 1548 |
| E4 | EHEC O157:H7 | 43890 | $10^{-5}$ | 1159 | 1711 |
| E5 | EHEC O157:H7 | 3000372 | $10^{-5}$ | 157 | 368 |
| E6 | EHEC unknown | 3000401 | $10^{-5}$ | 0 | 0 |
| E7 | EHEC O157:H7 | 3000934 | $10^{-5}$ | 1896 | 2304 |
| E8 | EHEC O157:H7 | 3001296 | $10^{-5}$ | 2824 | 2913 |
| E9 | EHEC O157:H7 | 4000563 | $10^{-5}$ | 1077 | 1168 |
| E10 | EHEC O157:H7 | 5000515 | $10^{-5}$ | 2558 | 2637 |
| E11 | EHEC O157:H7 | 5000544 | $10^{-5}$ | 2115 | 2084 |
| E12 | EHEC O157:H7 | 5000662 | $10^{-5}$ | 2612 | 2528 |
| E13 | EHEC O157:H7 | 5000936 | $10^{-5}$ | 2678 | 2664 |
| E14 | EHEC O157:H7 | 7000896 | $10^{-5}$ | 2307 | 2014 |
| E15 | EHEC O157:H7 | 7001111 | $10^{-5}$ | 3289 | 3260 |
| E16 | EHEC O157:H7 | 7001213 | $10^{-5}$ | 2915 | 2796 |
| E17 | EHEC O157:H7 | 8000541 | $10^{-5}$ | 1967 | 1692 |
| E18 | EHEC O157:H7 | 8000991 | $10^{-5}$ | 2394 | 2229 |
| E19 | EHEC O157:H7 | 9000134 | $10^{-5}$ | 2726 | 2544 |
| E20 | EHEC O157:H7 | 9000432 | $10^{-5}$ | 2292 | 2366 |
| E21 | EHEC O157:H7 | 9000784 | $10^{-5}$ | 2272 | 2230 |
| E31 | EHEC O157:H7 | | $10^{-6}$ | 245 | 230 |
| E32 | EHEC O157:H7 | | $10^{-6}$ | 314 | 313 |
| E33 | EHEC O157:H7 | | $10^{-6}$ | 319 | 321 |
| E34 | EHEC O157:H7 | | $10^{-6}$ | 284 | 278 |
| E35 | EHEC O157:H7 | | $10^{-6}$ | 311 | 311 |
| E36 | EHEC O157:H7 | | $10^{-6}$ | 349 | 415 |
| E37 | EHEC O157:H7 | | $10^{-6}$ | 255 | 282 |
| E38 | EHEC O157:H7 | | $10^{-6}$ | 513 | 439 |
| E39 | EHEC O157:H7 | | $10^{-6}$ | 306 | 383 |
| E40 | EHEC O157:H7 | | $10^{-6}$ | 280 | 252 |
| E41 | EHEC O157:H7 | | $10^{-6}$ | 330 | 277 |

TABLE 6

Exclusivity for RAPID-B *E. coli* O157 assay

| Stock # | Bacterial species or serotype | Ref. # | Dilution | Instrument 1 Run 1 (# cells) | Instrument 1 Run 2 (# cells) | Instrument 2 Run 1 (# cells) | Instrument 2 Run 2 (# cells) |
|---|---|---|---|---|---|---|---|
| S1 | Salmonella Typhimurium | 14028 | $10^{-5}$ | 1 | | 1 | 1 |
| S2 | S. Diarizonae | 299934 | $10^{-5}$ | 2 | | 0 | 0 |
| S3 | S. Gaminara | SEA 2575 | $10^{-5}$ | 1 | | 0 | 0 |
| S4 | S. Senftenberg | 43845 | $10^{-5}$ | 1 | | 0 | 0 |
| S5 | S. Stanley | H125C | $10^{-5}$ | 2 | | 2 | 1 |
| S6 | S. Montevideo | G4639 | $10^{-5}$ | 0 | 1 | 1 | 0 |
| S7 | S. Anatum | H3536 | $10^{-5}$ | 2 | | 0 | 1 |
| S8 | S. Infantis | H3517 | $10^{-5}$ | 0 | | 1 | 0 |
| S9 | S. Gaminara | F2712 | $10^{-5}$ | 0 | | 2 | 0 |
| S10 | S. Cubana | H7976 | $10^{-5}$ | 0 | | 0 | 1 |
| S11 | S. Montevideo | 8387 | $10^{-5}$ | 1 | | 0 | 1 |
| S12 | S. Paratyphi A | 11511 | $10^{-5}$ | 0 | | 0 | 1 |
| S13 | S. Paratyphi B | 8759 | $10^{-5}$ | 0 | | 1 | 0 |
| S14 | S. Enteritidis | 13076 | $10^{-5}$ | 2 | | 0 | 2 |
| S15 | S. Newport | 6962 | $10^{-5}$ | 0 | | 0 | 2 |
| S16 | S. Anatum | 9270 | $10^{-5}$ | 0 | | | |
| S17 | S. Kentucky | | $10^{-5}$ | 0 | | | |
| S18 | S. Minnesota | | $10^{-5}$ | 0 | | | |
| S19 | S. Hadar | | $10^{-5}$ | 0 | | | |
| S20 | S. Saintpaul | | $10^{-5}$ | 0 | | | |
| S21 | S. Agona | | $10^{-5}$ | 0 | | | |
| S22 | S. Derby | | $10^{-5}$ | 0 | | | |
| E1 | E. coli | DH5 Alpha | $10^{-5}$ | 0 | | | |
| LM1 | Listeria monocytogenes | 19115 | $10^{-5}$ | 3 | 1 | | |
| L1 | L. ivanovii | 19119 | $10^{-5}$ | 4 | 2 | | |
| L2 | L. innocua | 33090 | $10^{-5}$ | 3 | 0 | | |
| M1 | Staphylococcus aureus | 25923 | $10^{-5}$ | 1 | | | |
| M2 | Citrobacter diversus | KM 11012 | $10^{-5}$ | 3 | 1 | | |
| M6 | Pseudomonas aeruginosa | 9027 | $10^{-5}$ | 1 | | | |
| M7 | Shigella sonnei | 8000692 | $10^{-5}$ | 1 | | 0 | 0 |
| M8 | S. sonnei | 9000610 | $10^{-5}$ | | | 0 | 0 |

TABLE 6-continued

Exclusivity for RAPID-B *E. coli* O157 assay

| | | | | Instrument 1 | | Instrument 2 | |
|---|---|---|---|---|---|---|---|
| Stock # | Bacterial species or serotype | Ref. # | Dilution | Run 1 (# cells) | Run 2 (# cells) | Run 1 (# cells) | Run 2 (# cells) |
| M9 | *S. flexneri* | 9000946 | $10^{-5}$ | | | 0 | 0 |
| M10 | *S. flexneri* | 9000957 | $10^{-5}$ | | | 0 | 0 |
| M11 | *S. sonnei* | 9000958 | $10^{-5}$ | | | 0 | 0 |

This panel of exclusivity results was obtained by the ADH. Studies conducted in three other laboratories have looked at exclusivity for a much larger number of non-O157 *E. coli* isolates. These studies found no activity toward the reagents and no signals for any *E. coli* not having the O157 serotype.

The RAPID-B intrinsic LOD for *E. coli* O157, in CFUs, was <0.5 CFU/ml. That is, the RAPID-B analysis was more sensitive than spiking of an equivalent volume onto agar plates. This was the case whether the plating medium was plate count agar (PCA) or sorbitol-MacConkey agar (SMAC), the latter of which is normally specified for *E. coli* O157 growth. A possible explanation for such sensitivity resides in the phenomenon of viable but nonculturable bacterial cells. In this case, viable but non-culturable *E. coli* O157 cells were counted correctly by RAPID-B but not by agar plating.

The 0.5 CFU/ml LOD was consistent with linearity plots comparing plate CFUs and RAPID-B viable cell counts. FIG. 10 plots a typical linearity curve for dilutions of E3 (ADH clinical isolate #3000372, a strain of *E. coli* O157:H7). Over a two-month period, samples were co-analyzed on three RAPID-B instruments and the cell counts were compared to PCA- or SMAC-determined CFUs.

The RAPID-B linear dynamic range exceeded 4 orders of magnitude, beginning at single cell counts. The coefficient of regression, $R^2$, for RAPID-B live cell counts to average agar plate CFUs for a 10-plate array exceeded 0.99. The BAM surface plate method gave a false negative (no CFUs formed) in one case for a low level (single digit) spike, for a failure rate of about 5% at that level. RAPID-B was correct in all cases.

Instrumental drift (signal intensity from degradation of photomultipliers with time or use) was not observed. Such instrumental drift was simulated by introduction of a neutral density filter into the cytometer's detection optics. The multiplier voltage was increased to compensate for the reduced signal. Using the data acquisition protocol modified only for increased photomultiplier gain, the instrument still produced accurate enumeration when compared to agar plate CFUs.

Competitive organism experiments, using *Salmonella typhimurium* with *E. coli* O157 spiked into ground beef, showed RAPID-B cell counts (98.3±15.0, n=3) lower than, but within the same range as, those for corresponding low level experiments in which no competitive organism was added (131.8±27.8, n=9). In a similar experiment, spiking with *Salmonella typhimurium* alone did not produce false positive results. This result for ground beef was consistent with those in the exclusivity panel, for which potential confounding or synergistic food matrix effects were not evaluated.

Validation to FERN 2 Specifications of RAPID-B *E. coli* O157 Assay in Nine Foods Following the Food Emergency Response Network (FERN) Level 2 method validation specifications, the studies involved qualitative analysis for *E. coli* O157, comparing results for parallel analyses by RAPID-B and the FDA BAM. There were two levels of spiking into the nine different foods previously listed. The BAM method, even after overnight enrichment, often failed when the inoculation level was low (about 0.3 CFU/g) and the cells were stressed, either by refrigeration or by the previously described endogenous or added growth inhibitors. On parallel analyses, the RAPID-B method never failed, regardless of low spiking levels and inherent food or refrigeration-induced stress. The RAPID-B and BAM methods agreed and were consistently correct for spiking into fresh spinach.

Table 7 contains results from spiking onto 25 g of jalapeño peppers. BAM used mTSB-n; RAPID-B used TSB. Numbers for RAPID-B runs represent cell counts in a 100 µL analyzed volume for a $10^{-4}$ dilution of the broth. The data show multiple failures (Table 7 cells with shaded background) at the low inoculation level for the BAM method vs. the corresponding entries demonstrating consistent accuracy of the RAPID-B assay.

TABLE 7

Product testing by BAM 4a and RAPID-B for spikes of jalapeño peppers with overnight growth in 225 mL of broth.

| Sample ID | Approx. inoculation BAM Samples | BAM Final Conclusion | Approx. inoculation LRB* Samples | RAPID-B Final Conclusion | LRB run 1 | LRB run 2 | LRB run 3 |
|---|---|---|---|---|---|---|---|
| P-1 | 0 | − | 0 | − | 0 | 0 | 0 |
| P-2 | 20 | ▓ | 25 | + | 113 | 107 | 129 |
| P-3 | 200 | + | 250 | + | 395 | 475 | 371 |
| P-4 | 0 | − | 0 | − | 0 | 0 | 0 |
| P-5 | 20 | ▓ | 25 | + | 285 | 319 | 355 |
| P-6 | 200 | + | 250 | + | 431 | 463 | 437 |
| P-7 | 0 | − | 0 | − | 0 | 0 | 0 |
| P-8 | 20 | ▓ | 25 | + | 266 | 298 | 299 |
| P-9 | 200 | + | 250 | + | 398 | 435 | 456 |
| P-10 | 0 | − | 0 | − | 1 | 0 | 0 |
| P-11 | 20 | + | 25 | + | 100 | 150 | 107 |
| P-12 | 200 | + | 250 | + | 611 | 624 | 650 |
| P-13 | 0 | − | 0 | − | 0 | 0 | 0 |
| P-14 | 20 | + | 25 | + | 50 | 44 | 36 |
| P-15 | 200 | + | 250 | + | 365 | 379 | 320 |
| P-16 | 0 | − | 0 | − | 0 | 0 | 0 |
| P-17 | 20 | ▓ | 25 | + | 103 | 102 | 93 |
| P-18 | 200 | + | 250 | + | 446 | 605 | 573 |
| P-N | 0 | − | 0 | − | 0 | 0 | 0 |

*LRB = Litmus RAPID-B.

RAPID-B counts in Runs 1-3 of Table 7 show a semi-quantitative relationship to the initial spiking level. They were not accurate enough to infer initial cell concentration because of differential growth rate depression attributable to a non-controlled variable: the number of background microflora in each jalapeño pepper sample. In an incurred residue sample, another inferential limitation would be delay of the log phase due to environmental stress.

First step growth selectivity/universality and food sample identity were the experimental variables that distinguished consistent RAPID-B success from a significant percentage of BAM failures. The correct results were obtained at both inoculation levels by both methods in most foods, in agreement with Weagant and Bound (*Int. J. Food Microbiol.* 71:87-92, 2001), who found that selective liquid culture alone did not necessarily compromise BAM results. However, when low cell numbers were stressed by the food matrix (by capsaicin in jalapeño peppers or disinfectants added to some brands of bagged salads), recovery from overnight culture in mTSB-n proved erratic.

Analysis after Recovery from Ground Beef and Short-Term Growth

Considering time economies from batch centrifugation, the average time from the end of the 5 hour incubation to the beginning of instrumental analysis was only 8 minutes per sample. To increase system sensitivity, the larger analyzed volume of 200 µL was used. Analyzing at 100 µL per minute, and allowing 30 seconds for drawing up each sample plus three flush cycles between samples to eliminate carryover, the total period between analyses was 4 minutes. With a 5 hour incubation and preparation/analysis taking 8+4=12 minutes per sample, the TTR for ground beef analysis was 5 hours 12 minutes.

The performance results obtained included average raw counts for blank samples of 0.8±0.8 (n=12). Based on this, it was possible to establish a threshold of average blank plus $3\sigma=0.8+2.4=3.2$ or, being conservative, 4 counts. This threshold yielded a >99% probability of avoiding false positive results. Raw counts for low-level inoculation after 5 h of growth and the indicated sampling procedures averaged 322.3. Calculating the C/T as average counts less average background divided by threshold, (322.3−0.8)/4 gave 80, for a nominal initial inoculation of only five viable cells in the ground beef. Had the initial inoculation constituted of a single viable *E. coli* O157 cell, assuming the same lag phase duration and growth rate, these results would project a cell count of 64 with a C/T>16. For the inoculation levels in these experiments, 100% of the RAPID-B analyses were correct, whether the inoculation was blank, low positive or high positive. Parallel analyses, per BAM 4a, with selective first-stage overnight growth, showed a single false negative result for one of the low-level positives. This represented a 6% failure rate by the reference method.

CONCLUSIONS

The RAPID-B *E. coli* O157 assay was independently validated to FERN 2 standards for inclusivity (41 isolates), exclusivity (many isolates of non-O157 *E. coli* and 33 strains from other genera), and insensitivity to competing microflora. It exhibited significantly greater sensitivity than plate count methods for detection of low-level contamination (intrinsic LOD, 0.6 CFU) as well as counting equivalence for sample co-analysis on multiple instruments. Quantitative results established a four order of magnitude linear dynamic range ($R^2=0.999$) compared to results from two different media in 10-plate arrays. Assay qualitative validation at three inoculation levels was 100% successful in all nine food products. The method validation reported here used an overnight grow-out for direct comparison to the reference (BAM) method for *E. coli* O157. Even for the lowest inoculated samples, overnight growth produced $>10^6$ CFUs/mL. Due to RAPID-B's inherent sensitivity of <1 CFU/mL, samples were diluted by three to four orders of magnitude for analysis.

Such a sensitive technique does not require overnight grow-out to produce results, and this indicates that a significantly shorter enrichment time can be used. That is, if enrichment is necessary to obtain results (e.g., food product testing with a 1 CFU/25 g of product detection requirement). For the 1 CFU in 25 g of product detection requirement, it is highly desirable to obtain an answer in less time than an 8 hour job shift. This is the reason for the short period enrichment used for the *E. coli* O157 in ground beef experiment that was reported.

For RAPID-B analysis of *E. coli* O157 in ground beef, a standard operating procedure was determined for detection after a 5 hour growth of as few as five O157 cells in 25 g of product. RAPID-B was 100% accurate. The projected RAPID-B LOD was a single viable cell with S/T>16 and a TTR of 5 hours 12 minutes. Parallel analyses by overnight culture plating had a 6% failure rate.

REFERENCES

Anonymous, 2009. *Escherichia coli* O157:H7 in prepackaged Nestlé Toll House refrigerated cookie dough. *Expert Rev. Anti-Infective Ther.* 7, 641.

AOAC International, 2006. Final Report and Executive Summaries from the AOAC International presidential task force on best practices in microbiological methodology. www-.fda.gov/ucm/groupfds/fdagov-publid@fdagov-foods-gen/documents/document/ucm088702.pdf.

Berdalet, E., Dortch, Q., 1991. New double-staining technique for RNA and DNA measurement in marine phytoplankton. Mar. Ecol. Prog. Ser., 73, 267-274.

Centers for Disease Control and Prevention, 2006. Ongoing multistate outbreak of *Escherichia coli* serotype O157:H7 infections associated with consumption of fresh spinach—United States. Morbid. Mortal. Weekly Rep. 55, 1045-1046.

Cleary, 2004. The role of Shiga-Toxin producing *Escherichia coli* in hemorrhagic colitis and hemolytic uremic syndrome. Sem. Pediatric Infect. Dis., 15, 260-265.

Cody et al., 1999. An outbreak of *Escherichia coli* O157:H7 infection from unpasteurized commercial apple juice. *Ann. Intern. Med.* 130, 202-209.

Comas, J, Vives-Rego, J., 1998. Enumeration, viability and heterogeneity in *Staphylococcus aureus* cultures by flow cytometry. *J. Microbiol. Methods*, 32, 45-53.

Denny et al., 2008. Outbreak of *Escherichia coli* O157:H7 associated with raw milk consumption in the Pacific Northwest. *Foodb. Pathog. Dis.* 5, 321-328.

Green, B. R., Durnford, D. G., 1996. The chlorophyll-carotenoid proteins of oxygenic photosynthesis. *Annu. Rev. Plant Physiol. Plant Mol. Biol.* 47:685-714.

Feng et al., 2011. Bacteriological Analytical Manual, Chapter 4a—Diarrheagenic *Escherichia coli* O157:H7. Food and Drug Administration, www.fda.gov/food/foodsafety/foodborneillness/foodborneillnessfoodbornepatho gensnaturaltoxins/badbugbook/ucm071284.htm.

Food and Drug Administration, 2009[a]. Bad Bug Book BBB—*Escherichia coli* O157:H7 (EHEC) Updated: Jul. 10, 2009 www.fda.gov/food/foodsafety/foodborneillness/foodborneillnessfoodbornepathoge nsnaturaltoxins/badbugbook/ucm071284.htm Food and Drug Administration, 2009b. Bacteriological Analytical Manual, 8th Edition, Revision A, 1998. Updated:

May 14, 2009. www.fda.gov/Food/ScienceResearch/LaboratoryMethods/BacteriologicalAnalyticalManual-BAM/default.htm Foote, 1971. Mechanism of addition of singlet oxygen to olefins and other substrates. *Pure and Applied Chem.* 27, 635-645.

Green and Durnford, 1996. The Chlorophyll-Carotenoid Proteins of Oxygenic Photosynthesis, *Annu. Rev. Plant Physiol. Plant Mol. Biol.* 47, 685-714.

Hedhammar et al., 2005. A novel flow cytometry-based method for analysis of expression levels in *Escherichia coli*, giving information about precipitated and soluble protein. *J. Biotechnol.* 119, 133-146.

Henery et al., 2008. Quantitative image based apoptotic index measurement using multispectral imaging flow cytometry: a comparison with standard photometric methods. *Apoptosis* 13:1054-1063.

Koohmaraie et al., 2007. Interventions to reduce/eliminate *Escherichia coli* O157:H7 in ground beef. *Meat Sci.* 77, 90-96.

Kusunoki et al., 2000. Flow cytometry for the detection of enterohaemorrhagic *Escherichia coli* O157:H7 with latex beads sensitized with specific antibody. *J. Vet. Med. B* 47, 551-559.

McCarthy, 1996. *E. coli* O157:H7 outbreak in USA traced to apple juice. *Lancet* 348, 1299.

McGrath, 2006. Food Emergency Response Network Method Development/Validation/Harmonization. US Food and Drug Administration. www.flworkshop.com/2006/P4-McGrath_Tim.pdf Muirhead, 1984. Applications of flow cytometry in clinical diagnosis. *Trends In Analytical Chemistry*, 3, 107-111.

Lindqvist, 1997. Preparation of PCR samples from food by a rapid and simple centrifugation technique evaluated by detection of *Escherichia coli* O157:H7. *Int. J. Food Microbiol.* 37, 73-82.

Owens et al., 2009. FERN Level 2 Validation: Assessment of the LITMUS RAPID-B *E. coli* O157 Assay with Nine Product Matrices. Available in Supplementary Materials, Wilkes et al., Reduction of food matrix interference by a combination of sample preparation and multidimensional gating techniques to facilitate rapid, high sensitivity analysis for *Escherichia coli* serotype O157 by flow cytometry, *Food Microbiology* (2011), doi:10.1016/j.fm.2011.11.002

Rossen et al., 1992. Inhibition of PCR by components of food samples, microbial diagnostic assays and DNA-extraction solutions. *Int. J. Food Microbiol.* 17: 37-45.

Sandvig, 2001. Shiga Toxins. *Toxicon,* 39, 1629-1635.

Snedeker et al., 2009. Primary and secondary cases in *Escherichia coli O*157 outbreaks: a statistical analysis. *BMC Infect. Dis.* 9, 144.

Steen, 2000. Flow cytometry of bacteria: glimpses from the past with a view to the future. *J. Microbiol. Meth.* 42, 65-74.

Stevens and Jaykus, 2004. Bacterial separation and concentration from complex sample matrices: A review. *Crit. Rev. Microbiol.* 30, 7-24.

Taylor et al., 2005. Effect of food matrix and cell growth on PCR-based detection of *Escherichia coli* O157:H7 in ground beef. *J. Food Prot.* 68, 225-232.

Tortorello et al., 1998. Quantitative analysis and isolation of *Escherichia coli* O157:H7 in a food matrix using flow cytometry and cell sorting. *FEMS Immunol. Med. Microbiol.* 19, 267-274.

Uyttendaele et al., 1999. Evaluation of buoyant density centrifugation as a sample preparation method for NASBA-ELGA detection of *Campylobacter jejuni* in foods. *Food Microbiol.* 16, 575-582.

Weagant et al., 1995. An improved rapid technique for isolation of *Escherichia coli* O157:H7 from foods. *J. Food Prot.,* 58, 7-12.

Weagant and Bound, 2001. Evaluation of techniques for enrichment and isolation of *Escherichia coli* O157:H7 from artificially contaminated sprouts. *Int. J. Food Microbiol.* 71, 87-92.

Wilkes et al., 2012. Reduction of food matrix interference by a combination of sample preparation and multi-dimensional gating techniques to facilitate rapid, high sensitivity analysis for *Escherichia coli* serotype O157 by flow cytometry. *J. Food Microbiol.* 30, 281-288.

Yang et al., 2010. Rapid, absolute, and simultaneous quantification of specific pathogenic strain and total bacterial cells using an ultrasensitive dual-color flow cytometer. *Anal. Chem.* 82, 1109-1116.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method of detecting one or more target bacteria in a test sample comprising:
   incubating the test sample in a bacterial culture medium that permits growth of bacteria present in the test sample;
   contacting the bacterial culture medium containing the test sample with a photosensitizing agent;
   exposing the bacterial culture medium containing the test sample to infra-red light, visible light, or UV light, under conditions sufficient for the photosensitizing agent to photobleach contaminating or autofluorescing non-bacterial particulates present in the sample;
   separating the bacteria from the bacterial culture medium containing the test sample, thereby generating an isolated bacterial sample;
   contacting the isolated bacterial sample with a specific binding agent specific for the one or more target bacteria, under conditions sufficient for the specific binding agent to bind to the one or more target bacteria, wherein the specific binding agent is directly or indirectly labeled;
   permitting detection of the labeled specific binding agent bound to the one or more target bacteria; and
   designating the test sample as containing the one or more target bacteria when the labeled specific binding agent bound to the one or more target bacteria is detected.

2. The method of claim 1, wherein the bacterial culture medium comprises brain heart infusion medium or tryptic soy broth.

3. The method of claim 1, wherein the incubation of the test sample is at 37° C. to 45° C. for at least 4 hours.

4. The method of claim 1, wherein the photosensitizing agent is phloxine B.

5. The method of claim 1, wherein the exposing the bacterial culture medium containing the test sample to the light comprises the bacterial culture medium containing the test sample to a light intensity of at least 10,000 LUX.

6. The method of claim 1, wherein the separating the bacteria from the bacterial culture medium containing the test sample comprises pelleting the bacteria.

7. The method of claim 1, wherein the separating the bacteria from the bacterial culture medium containing the test sample comprises filtering the bacterial culture medium one or more times.

8. The method of claim 1, wherein the separating the bacteria from the bacterial culture medium containing the test sample comprises centrifuging the bacterial culture medium.

9. The method of claim 1, wherein the method further comprises contacting the isolated bacterial sample with one or more detergents or surfactants.

10. The method of claim 1, wherein the specific binding agent is directly or indirectly labeled with a fluorophore.

11. The method of claim 1, wherein the specific binding agent is directly labeled.

12. The method of claim 1, wherein the specific binding agent is indirectly labeled, and the method further comprises:

contacting the isolated bacterial sample with a secondary agent specific for the specific binding agent, under conditions sufficient for the secondary agent to bind to the specific binding agent.

13. The method of claim 1, wherein the specific binding agent is an antibody, peptide nucleic acid (PNA) or an aptamer.

14. The method of claim 12, wherein the secondary agent is a labeled secondary antibody.

15. The method of claim 1, wherein the method further comprises:

determining whether the one or more target bacteria detected in the sample are alive or dead.

16. The method of claim 1, wherein the detecting the one or more target bacteria occurs before the photobleaching deteriorates cell membranes and cell surface epitopes of the one or more target bacteria.

17. The method of claim 1, wherein the sample is a food sample, patient sample, or environmental sample.

18. The method of claim 1, wherein the method is completed in 4 hours to 8 hours.

* * * * *